United States Patent
Smith et al.

(10) Patent No.: US 8,426,568 B2
(45) Date of Patent: Apr. 23, 2013

(54) RHAMNOSE SUBSTITUENTS OF SL0101 AND THERAPEUTIC USES THEREOF

(75) Inventors: Jeffrey A. Smith, Earlysville, VA (US); Sidney M. Hecht, Charlottesville, VA (US); Deborah A. Lannigan-Macara, Charlottesville, VA (US); David J. Maloney, Point of Rocks, MD (US)

(73) Assignee: University of Virginia Patent Foundation, Charlottesville, VA (US)

( * ) Notice: Subject to any disclaimer, the term of this patent is extended or adjusted under 35 U.S.C. 154(b) by 863 days.

(21) Appl. No.: 12/301,656

(22) PCT Filed: May 22, 2007

(86) PCT No.: PCT/US2007/012156
§ 371 (c)(1),
(2), (4) Date: Sep. 9, 2009

(87) PCT Pub. No.: WO2007/139778
PCT Pub. Date: Dec. 6, 2007

(65) Prior Publication Data
US 2010/0016245 A1      Jan. 21, 2010

Related U.S. Application Data

(60) Provisional application No. 60/802,313, filed on May 22, 2006.

(51) Int. Cl.
*C07H 17/07* (2006.01)
*A61K 31/7048* (2006.01)

(52) U.S. Cl.
USPC .............................................. 536/8; 514/27

(58) Field of Classification Search ......... 536/8; 514/27
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,733,523 A | 3/1998 | Kuijpers et al. |
| 5,910,583 A | 6/1999 | Marks et al. |
| 6,372,719 B1 | 4/2002 | Cunningham et al. |
| 2003/0125265 A1 | 7/2003 | Hung et al. |
| 2004/0023992 A1 | 2/2004 | Das et al. |
| 2005/0233985 A1 | 10/2005 | Smith et al. |
| 2007/0049539 A1 | 3/2007 | Smith et al. |

FOREIGN PATENT DOCUMENTS

| | | |
|---|---|---|
| WO | WO99/34015 | 7/1999 |
| WO | WO03/005766 | 12/2003 |
| WO | WO2006/086103 | 8/2006 |

OTHER PUBLICATIONS

FDA Guidance for Industry on Container Closure Systems for Packaging Human Drugs and Biologics, May 1999.*
Smith et al., Bioorg. Med. Chem., 2006, 14, p. 6034-6042.*
International Search Report/Written Opinion for PCT/US2007/012156 completed Sep. 24, 2007.
Maloney, David Joseph, "Synthesis of Biologically Active Phenolic Natural Products", University of Virginia, Department of Chemistry, Aug. 2005, Table of Contents and Abstract.
Maloney, David J., et al., "Synthesis of a Potent and Selective Inhibitor of p90 RSK", 2005, *American Chemical Society*, vol. 7, No. 6, pp. 1097-1099.
Nguyen, Tam Luong, et al., "Homology Model of RSK2 N-Terminal Kinase Domain, Structure-Based Identification of Novel RSK2 Inhibitors, and Preliminary Common Pharmacophore", 2006, *Bioorganic & Medicinal Chemistry*, No. 14, pp. 6097-6105.
Shan, Mingde, et al., "De Novo Asymmetric Syntheses of SL0101 and its Analogues Via a Palladium-Catalyzed Glycosylation", Aug. 22, 2006, *American Chemical Society*, Vo. 8, No. 22, pp. 5149-5152.
Smith, Jeffrey A., et al., "Structural Basis for the Activity of the RSK-Specific Inhibitor, SL0101", 2007, *Bioorganic & Medicinal Chemistry*, No. 15, pp. 5018-5034.
Xu, Ya-ming, et al., "Three Acetylated Flavonol Glycosides From Forsteronia Refracta That Specifically Inhibit p90 RSK", 2006, *Bioorganic & Medicinal Chemistry*, No. 14, pp. 3974-3977.
Cahn, R. S., et al., "Specification of Configuration about Quadricovalent Asymmetric Atoms", Received Nov. 30, 1950, *The Chemical Society*, pp. 612-622.
Cahn, R. S., et al., "The Specification of Asymmetric Configuration in Organic Chemistry", 1956, *Experientia*, vol. 12, No. 3, pp. 81-124.
Cahn, R. S., et al., "An Introduction to the Sequence Rule; A System for the Specification of Absolute Configuration", Mar. 1964, *The Chemical Society*, vol. 41, No. 3, pp. 116-125.
Cahn, R. S., et al., "Specification of Molecular Chirality", 1966, *Agnew. Chem. Internat. Edit.*, vol. 5, No. 4, pp. 385-415.
Cahn, R. S., et al., "Spezifikation der Molekularen Chiralitat", 1966, *Agnew. Chem..*, vol. 78, No. 8, pp. 413-447.
Clark, David E., et al., "Rsk2 Allosterically Activates Estrogen Receptor a by Docking to the Hormone-Binding Domain", 2001, *The EMBO Journal*, vol. 20, No. 13, pp. 3484-3494.
Clark, David E., et al., "The Serine/Threonine Protein Kinse, p90 Ribosomal S6 Kinase, Is an Important Regulator of Prostate Cancer Cell Proliferation", 2005, *Cancer Research*, vol. 65, No. 8, pp. 3108-3116.
Cohen, Michael S., et al., "Structural Bioinformatics-Based Design of Selective, Irreversible Kinase Inhibitors", May 27, 2005, *Science*, vol. 308, pp. 1318-1321.

(Continued)

*Primary Examiner* — Shaojia Anna Jiang
*Assistant Examiner* — Jonathan S Lau
(74) *Attorney, Agent, or Firm* — Barnes & Thornburg LLP

(57) ABSTRACT

The present invention provides compositions and methods useful for preparing and using analogs, derivatives, and modifications of kaempferols that have anti-neoplastic activity. More specifically, the compounds are analogs, derivatives, and modifications of SLO1O1. The invention further provides compounds that are inhibitors of rsk activity. The invention further provides compounds that selectively inhibit excessive rsk activity in cancers. The present invention further provides methods for treating cancer using compounds of the invention.

2 Claims, 7 Drawing Sheets

OTHER PUBLICATIONS

Cohen, Philip, "Protein Kinases—The Major Drug Targets of the Twenty-First Century?", Apr. 2002, *Nature Reviews*, vol. 1, pp. 309-315.

Dalby, Kevin N., et al., "Identification of Regulatory Phosphorylation Sites in Mitogen-Activated Protein Kinase (MAPK)-Activated Protein Kinase-1a/p90$^{RSK}$ That Are Inducible by MAPK", Jan. 16, 1998, *The Journal of Biological Chemistry*, vol. 273, No. 3, pp. 1496-1505.

David, Jean-Pierre, et al., "Essintial Role of RSK2 in C-Fos-Dependent Osteosarcoma Development", Mar. 2005, *The Journal of Clinical Investigation*, vol. 115, No. 3, pp. 664-672.

Davie, James R., "MSK1 and MSK2 Mediate Mitogen- and Stress-Induced Phosphorylation of Histone H3: A Controversy Resolved", Aug. 12, 2003, *Perspective*, No. 195, pp. 1-4.

Gribble, Fiona M., et al., "A Novel Method for Measurement of Submembrane ASTP Concentration", Sep. 29, 2000, *The Journal of Biological Chemistry*, vol. 275, No. 39, pp. 30046-30049.

Hurbin, Amandine, et al., "Cooperation of Amphiregulin and Insulin-Like Growth Factor-1 Inhibits Bax- and Bad-Mediated Apoptosis Via A Protein Kinase C-Dependent Pathway in Non-Small Cell Lung Cancer Cells", May 20, 2005, *The Journal of Biological Chemistry*, vol. 280, No. 20, pp. 19757-19767.

Peteranne B. Joel, et al., "PP90$^{RSK1}$ Regulates Estrogen Receptor-Mediated Transcription Through Phosphorylation if Ser-167", Apr. 1998, *Molecular and Cellular Biology*, vol. 18, No. 4, pp. 1978-1984.

Leighton, Ian A., et al., "Comparison of the Specificities of p70 S6 Kinase and MAPKAP Kinase-1 Identifies a Relatively Specific Substrate for p70 S6 Kinase: The N-Terminal Kinase Domain of MAPKAP Kinase-I Is Essential for Peptide Phosphorylation", 1995, *FEBS*, Letters 375, pp. 289-293.

Mills, Gordon B., et al., "Linking Molecular Therapeutics to Molecular Diagnostics: Inhibition of the FRAP/RAFT/TOR Component of the P13K Pathway Preferentially Blocks PTEN Mutant Cells in Vino and in Vivo", Aug. 28, 2001, *PNAS*, vol. 98, No. 18, pp. 10031-10033.

Morillo, Marielba, et al., "Synthesis of Peracetylated Chacotriose", 2001, *Carbohydrate Research*, vol. 334, pp. 281-287.

Neshart, Mehran S., et al., "Enhanced Sensitivity of PTEN-Deficient Tumors to Inhibition of FRAP/mTOR", Aug. 28, 2001, *PNAS*, vol. 98, No. 18, pp. 10314-10319.

Richards, Stephanie A., et al., "Ribosomal S6 Kinase 1 (RSK1) Activation Requires Signals Dependent on and Independent of the MAP Kinase ERK", Jul. 22, 1999, Current Biology, vol. 9, p. 810-820.

Rouz, Philippe P., et al., "ERK and p38 MAPK-Activated Protein Kinases: A Family of Protein Kinases with Diverse Biological Functions", Jun. 2004, *Microbiology and Molecular Biology Reviews*, vol. 68, No. 2, pp. 320-344.

Sebolt-Leopold, Judith S., "Development of Anticancer Drugs Targeting the MAP Kinase Pathway", 2000, *Oncogene*, vol. 19, pp. 6594-6599.

Smith, Jeffrey A., et al., "Identification of the First Specific Inhibitor of p90 Ribosomal S6 Kinase (RSK) Reveals an Unexpected Role for RSK in Cancer Cell Proliferation", 2005, *Cancer Research*, vol. 65, No. 3, pp. 1027-1034.

Soloaga, Ana, et al., "MSK2 and MSK Mediate the Mitogen- and Stress-Induced Phosphorylation of Histone H3 and HMG-14", 2003, *The EMBO Journal.*, vol. 22, No. 11, pp. 2788-2797.

Vik, Terry A., et al., "Identification of Serine 380 as the Major Site of Autophosphorylation of *Xenopus* pp90rsk", 1997, *Biochemical and Biophysical Research Communications*, vol. 235, pp. 398-402.

Xu, Ya-Ming, et al., "Three Acetylated Flavonol Glycosides From *Forsteronia* Refracta That Specifically Inhibit p90 RSK", 2006, *Bioorganic and Medicinal Chemistry*, vol. 14, pp. 3974-3977.

Wang, Xuemin, et al., "Regulation of Elongation Factor 2 Kinase by p90$^{RSK1}$ and p70 S6 Kinase", 2001, *The EMBO Journal*, vol. 20, No. 16, pp. 4370-4379.

Hardman, Joel G., et al., "Goodman and Gillman's The Pharmacological Basis of Therapeutics, 10$^{th}$ Edition", 2001, *McGraw-Hill*, Section 1, General Principles, pp. 54-57.

Koul, Anil, et al., "Interplay Between Mycobacteria and Host Signalling Pathways", Mar. 2004, *Nature Reviews, Microbiology*, vol. 2, pp. 189-202.

Matthes, H. W. D., et al., "Cytotoxic Components of Zingiber Zerumbet Curcuma Zedoaria and C. Domestica", 1980, *Phytochemistry*, vol. 19, pp. 2643-2650.

* cited by examiner

|  | R₁ | R₂ | R₃ |
| --- | --- | --- | --- |
| SL0101 (1) | OH | OAc | OAc |
| 2",4"-di-O-acetyl SL0101 | OAc | OH | OAc |
| 4"-mono-O-acetyl SL0101 | OH | OH | OAc |

RHAMNOSE SUBSTITUENTS OF SL0101 AND THERAPEUTIC USES THEREOF

CROSS REFERENCE TO RELATED APPLICATIONS

This application is a U.S. national counterpart application of international application serial no. PCT/US2007/012156 filed May 22, 2007, is entitled to priority pursuant to 35U.S.C. §119(e), to U.S. provisional patent application No. 60/802,313 filed on May 22, 2006, the entirety of which is incorporated by reference herein.

STATEMENT REGARDING FEDERALLY SPONSORED RESEARCH OR DEVELOPMENT

This work was supported in part by the Department of Defense, USAMRMC grant number DAMD17-03-1-0366. The United States Government therefore has certain rights in the invention.

BACKGROUND

The p90-kDa ribosomal S6 kinase (RSK) family members are downstream effectors of mitogen-activated protein kinase (MAPK). MAPK is known to be important in proliferation and oncogenesis.[2,3] However, it has only now become possible to distinguish the function of RSK in these processes from those of MAPK itself and of the many other downstream MAPK effectors because of the recent discovery of a RSK-specific inhibitor.[4] It was found that an extract from *Forsteronia refracta*, a member of the Apocynaceae (dogbane) family found in the South American rainforest, was able to specifically inhibit RSK catalytic activity.[4] Fractionation of the extract led to the isolation of an active component kaempferol 3-O-(3",4"-di-O-acetyl-α-L-rhamnopyranoside), also referred to as SL0101. SL0101 is competitive with respect to ATP with a dissociation constant, $K_i$, of 1 μM.[4] This compound is an effective and specific inhibitor of RSK in intact cells.[4] SL0101 inhibits proliferation of the human breast cancer cell line, MCF-7, with an efficacy paralleling its ability to inhibit RSK in intact cells. Significantly, SL0101 does not prevent the growth of the normal human breast line, MCF-10A, even though it inhibits RSK activity in these cells.[4]

It is known that RSK increases the transcriptional activity of estrogen receptor α (ERα) and the androgen receptor (AR).[5-7] Increased activity of ERα and AR are known to be important in the etiology of some breast and prostate cancers, respectively. Furthermore, it is known that RSK levels are higher in ~50% of human breast and prostate tumors compared to normal tissue.[4,7] Evidence from other laboratories has demonstrated that RSK is involved in osteosarcoma formation and in non-small cell lung carcinoma.[8,9] Taken together, these results suggest that RSK could serve as an important novel drug target in some types of cancers. Protein kinases have been shown to be excellent targets for drug discovery[10].

There is a long felt need in the art for compositions and methods useful for preventing and inhibiting cancer cell proliferation and for treating cancer in subjects in need thereof. The present invention satisfies these needs.

SUMMARY OF THE INVENTION

The present invention, as described in the disclosure provided herein, is based on the unexpected results that derivatives of SL0101 have greater cell proliferation inhibitory properties and greater ability for cellular uptake than SL0101. The summary, as well as the following detailed description of preferred embodiments of the invention, will be better understood when read in conjunction with the chemical structures and formulas provided herein. For the purpose of illustrating the invention, there are shown by chemical structures and formulas embodiments which are presently preferred. It should be understood, however, that the invention is not limited to the precise arrangements and instrumentalities provided herein.

In one aspect, compounds of the present invention are derivatives of the general structure having formula I (see also FIG. 1):

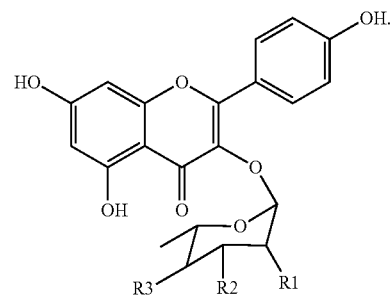

The known compound kaempferol 3-O-(3",4"-di-O-acetyl-α-L-rhamnopyranoside), referred to as SL0101, comprises OH at the R1 position, and OAc at the R2 and R3 positions of formula I (Xu et al., 2006, Biorg. Med. Chem., 14:3974-3977) (also see FIG. 1 herein).

The efficacy of SL0101 as an RSK inhibitor in intact cells is ~50-fold higher than its dissociation constant. Without wishing to be bound by any particular theory, based on the efficacy of SL0101 relative to its dissociation constant it was postulated herein that the potency of SL0101 in a cell could be limited by cellular uptake. Therefore, the present application discloses experiments demonstrating the preparation and use of more effective cancer cell inhibitors, which in some instances are more effective RSK-specific inhibitors, by synthesizing analogs that have a higher octanol-water partition coefficient, LogP, than SL0101. The calculated LogP was increased, for example, by either replacing the 3" and 4"-acetyl groups on the rhamnose with butyryl groups or substituting the 2"-hydroxyl group with an acetyl group. The syntheses of kaempferol 3-O-(3",4"-di-O-butyryl-α-L-rhamnopyranoside) (also referred to as Bu-SL0101 herein) and kaempferol 3-O-(2",3",4"-tri-O-acetyl-α-L-rhamnopyranoside) (also referred to as 3Ac-SL0101 herein) were performed as described in the examples.

It is disclosed herein that 3Ac-SL0101, like synthetic SL0101[11], is an effective and specific inhibitor of RSK activity in intact cells. Bu-SL0101 was modestly more potent at inhibiting MCF-7 proliferation than SL0101 but was not completely specific for RSK inhibition in intact cells. However, 3Ac-SL0101 was ~2-fold more effective in inhibiting the growth of MCF-7 cells than SL0101. Additionally, 3Ac-SL0101 retained the preferential ability to inhibit the growth of MCF-7 compared to MCF-10A cells.

The present invention encompasses, inter alia, acylated and butyryl derivatives of general formula I, which are effective inhibitors of cancer cell proliferation. In one embodiment of the invention, R1, R2, and R3 may be OH, butyryl, or OAc. In one aspect, at least two of R1, R2, and R3 are OAc. In another aspect, R1, R2, and R3 are OAc. In one aspect, at least one of R1, R2, and R3 is OAc and at least one is butyryl. In another aspect, at least two of R1, R2, and R3 are butyryl. In yet another aspect, each of R1, R2, and R3 are butyryl.

In one embodiment, the compounds of the invention inhibit RSK activity. In one aspect, inhibiting RSK activity inhibits cancer cell proliferation.

The present invention further encompasses the preparation and use of the novel compound 3Ac-SL0101 (kaempferol 3-O-(2",3",4"-tri-O-acetyl-α-L-rhamnopyranoside)), which has the structure:

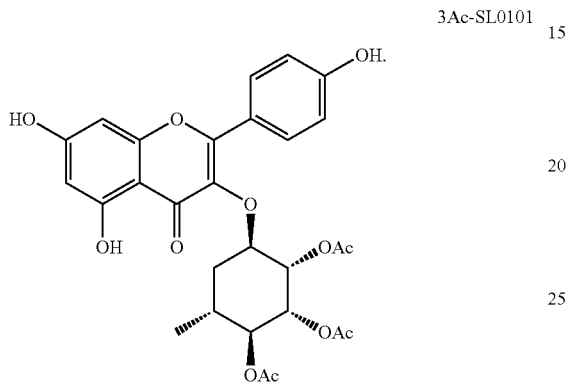

3Ac-SL0101

The present invention provides compositions and methods for preparing and purifying 3Ac-SL0101, and biologically active analogs and derivatives thereof. The present invention further provides methods for treating cancer by administering to a subject in need thereof a pharmaceutical composition comprising an effective amount of 3Ac-SL0101.

The present invention further encompasses the preparation and use of the novel compound kaempferol 3-O-(3",4"-di-O-butyryl-α-L-rhamnopyranoside) (also referred to as Bu-SL0101 herein). Bu-SL0101 has the structure:

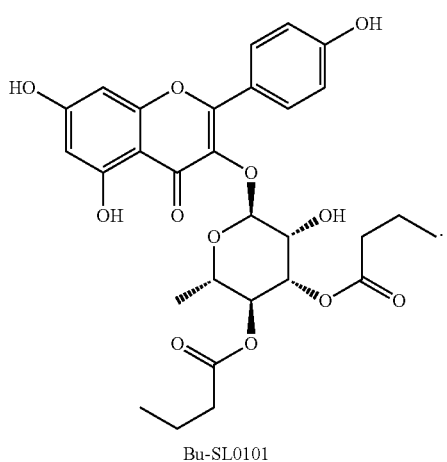 [SMILES: CCCC(=O)O[C@@H]1[C@@H](OC(=O)CCC)[C@@H](O)[C@H](Oc2c(-c3ccc(O)cc3)oc3cc(O)cc(O)c3c2=O)O[C@H]1C]

Bu-SL0101

The present invention provides compositions and methods for synthesizing and purifying Bu-SL0101 and biologically active analogs and derivatives thereof. The present invention further provides compositions and methods for administering to a subject in need thereof a pharmaceutical composition comprising an effective amount of Bu-SL0101, and biologically active analogs and derivatives.

The present invention further provides a compound having the structure of formula II:

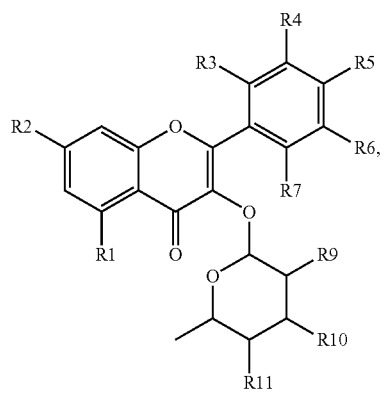

wherein R1, R2, R3, R4, R5, R6, and R7 are independently selected from the group consisting of OH, —OCOR8, —COR8, —SR8, and C1-C4 alkoxy;
R8 is H or C1-C4 alkyl; and
R9, R10, and R11 are independently selected from the group consisting of H, OH, —OCOR8, —COR8, —NHO-COR8, C1-C4 acyloxy, and C1-C4 alkoxy.

In one aspect of formula II, R9, R10, and R11 are each independently selected from the group consisting of OH, OAc, acetamide, and butyryl.

In another aspect of formula II, R1, R2, R3, R4, R5, R6, and R7 are each independently selected from the group consisting of OH and —SH.

The invention further encompasses compounds of formula II comprising combinations of OH, SH, OAc, acetamide, and butyryl as R groups The compounds comprised by formula II encompass replacing the hydroxyl groups (R1, R2, and/or R5) of the flavonoid with sulfhydryls (—SH) or adding sulfhydryls at positions R3, R4, R6, and/or R7. The compounds comprised by formula II further encompass replacing one or more acetyl groups on the sugar (R9, R10, and R11) with an acetamide (NHOCOH), on a compound such as 3Ac-SL0101. The acetamide can be a substituted acetamide comprising NHO-COR8. In one aspect, the compounds encompassed by formula II have greater stability in their interaction with RSK than does SL0101 in its interaction with RSK. In one aspect, the compounds encompassed by formula II maintain the important LogP similar to that of 3Ac-SL0101 and stabilize the essential hydrogen bonding substituents of the rhamnose. In another aspect, the compounds of formula II have a greater ability to inhibit RSK in an intact cell than does SL0101.

In one aspect, addition of acetamide to a compound of formula II helps to ensure that at least one essential group remains on the rhamnose because the acetamide will not be hydrolyzed in the cell. Replacing an acetyl with acetamide can reduce the hydrophobic character of the compound. Similarly, the addition of a sulfhydryl group to the flavonoid constituent can help maintain the hydrophobic character of the resulting compound similar to that of 3Ac-SL0101.

In one embodiment, the compounds of the invention inhibit cell proliferation. In one aspect, the cell is a cancer cell. In one aspect, the cancer cell is selected from the group consisting of a sarcoma, a prostate cancer cell, and a breast cancer cell.

In one embodiment, a compound of the invention inhibits excessive RSK activity. In one aspect, a compound of the invention inhibits excessive RSK activity with a greater efficacy than does SL0101.

In one embodiment, the cellular uptake of a compound of the invention is greater than the uptake of SL0101.

In one embodiment, the present invention encompasses a method of treating cancer in a subject in need thereof, comprising administering to a subject a pharmaceutical composition comprising an effective amount of at least one compound of the invention and a pharmaceutically-acceptable carrier.

In another embodiment, the present invention encompasses a method for treating a disease characterized by excessive RSK activity, comprising the step of administering to a subject in need thereof, a pharmaceutical composition comprising an effective amount of at least one compound represented by the general structure of formula I:

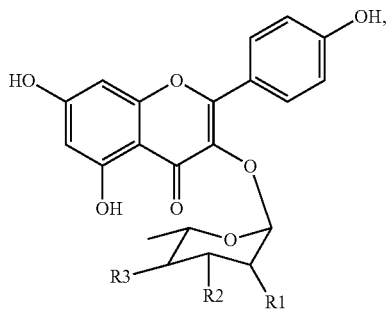

wherein R1, R2, and R3 are each independently selected from the group consisting of OH, OAc, and butyryl. In one aspect, R1, R2, and R3 are OAc. In another aspect, R2 and R3 are butyryl. In one aspect, R1, R2, and R3 are each butyryl. In another aspect, at least one of R1, R2, and R3 is OAc and at least one of R1, R2, and R3 is butyryl. In another aspect, R1 is OH. The invention further encompasses combinations of OAc and butyryl as R groups. In another embodiment, a compound of formula II is used. One of ordinary skill in the art will appreciate that a compound of the invention can also be administered with other therapeutic agents, as well as with different compounds of the invention.

In one embodiment, the disease is cancer. In one aspect, the cancer is selected from the group consisting of sarcoma, prostate cancer, and breast cancer. In one embodiment, the compound used to treat the disease characterized by excessive Rsk activity inhibits cell proliferation.

The present invention further encompasses the use of kits for administering at least one compound of the invention to a subject in need thereof.

DETAILED DESCRIPTION

Abbreviations and Acronyms

Figure 1:
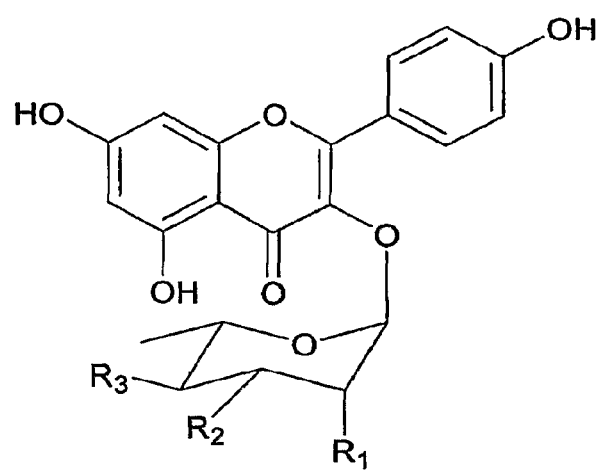
FIG. 1. Structures of SL0101, 2",4"-di-O-acetyl-SL0101 and 4"-mono-O-acetyl-SL0101.

| | |
|---|---|
| br- | broad |
| CTKD- | C-terminal kinase domain |
| CREB- | cyclic adenosine monophosphate response element binding protein |
| d- | doublet |
| dd- | doublet of doublets |
| DTT- | dithiothreitol |
| eEF2- | eukaryotic elongation factor 2 |
| EF2K- | EF2 kinase |
| GST- | Glutathione-S-transferase |
| MAPK- | mitogen-activated protein kinase |
| m- | multiplet |
| NTKD- | N-terminal kinase domain |
| PDB - | phorbol dibutyrate |
| PKA- | protein kinase A |

| | | |
|---|---|---|
| PKC- | protein kinase C | |
| q- | quartet | |
| RSK- | a 90 kDa ribosomal S6 kinase, also referred to as p90Rsk herein | |
| s- | singlet | |
| t- | triplet | |

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section.

The articles "a" and "an" are used herein to refer to one or to more than one (i.e. to at least one) of the grammatical object of the article. By way of example, "an element" means one element or more than one element.

As used herein, the term "affected cell" refers to a cell of a subject afflicted with a disease or disorder, which affected cell has an altered phenotype relative to a subject not afflicted with a disease or disorder.

Cells or tissue are "affected" by a disease or disorder if the cells or tissue have an altered phenotype relative to the same cells or tissue in a subject not afflicted with a disease or disorder.

As used herein, an "agonist" is a composition of matter which, when administered to a mammal such as a human, enhances or extends a biological activity attributable to the level or presence of a target compound or molecule of interest in the mammal.

An "antagonist" is a composition of matter which when administered to a mammal such as a human, inhibits a biological activity attributable to the level or presence of a compound or molecule of interest in the mammal.

A disease or disorder is "alleviated" if the severity of a symptom of the disease or disorder, the frequency with which such a symptom is experienced by a patient, or both, are reduced.

As used herein, "amino acids" are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

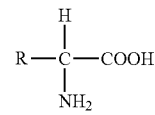

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

As used herein, an "analog" of a chemical compound is a compound that, by way of example, resembles another in structure but is not necessarily an isomer (e.g., 5-fluorouracil is an analog of thymine).

"Anti-proliferative," as used herein, refers to the ability of a compound to impede or inhibit cell proliferation. As such, the compound may act directly on a cell or may act indirectly. For example, in the context of cancer, a cancer cell can be inhibited from proliferating by depriving it of blood supply.

The term "anti-proliferative" does not refer to a particular mechanism by which proliferation is inhibited or impeded.

The term "biological sample," as used herein, refers to samples obtained from a subject, including, but not limited to, skin, hair, tissue, blood, plasma, cells, sweat and urine.

The term "cancer" as used herein is defined as proliferation of cells whose unique trait—loss of normal controls—results in unregulated growth, lack of differentiation, local tissue invasion, and metastasis. Examples include but are not limited to, breast cancer, prostate cancer, ovarian cancer, cervical cancer, skin cancer, pancreatic cancer, colorectal cancer, renal cancer and lung cancer.

The terms "cell," "cell line," and "cell culture" as used herein may be used interchangeably. All of these terms also include their progeny, which are any and all subsequent generations. It is understood that all progeny may not be identical due to deliberate or inadvertent mutations.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

A "compound," as used herein, refers to any type of substance or agent that is commonly considered a drug, or a candidate for use as a drug, as well as combinations and mixtures of the above.

As used herein, a "derivative" of a compound refers to a chemical compound that may be produced from another compound of similar structure in one or more steps, as in replacement of hydrogen by an alkyl, acyl, or amino group.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount" means an amount sufficient to produce a selected effect. For example, an effective amount of an RSK inhibitor is an amount of the inhibitor sufficient to, inter alia, suppress RSK activity in a serine/threonine kinase assay. An "effective amount" or "therapeutically effective amount" of a compound is that amount of compound which is sufficient to produce a selected or desired effect. The term "effective amount" is used interchangeably with "effective concentration" herein.

The term "excessive RSK activity", as used herein, refers to an increase in RSK activity in a cell with a disease or disorder, relative to the amount of such RSK activity in an otherwise identical normal cell.

As used herein, the term "flavonoid" refers to polyphenolic compounds possessing a carbon skeleton having the general structure:

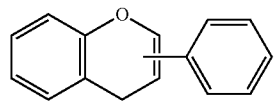

The terms "formula" and "structure" are used interchangeably herein.

As used herein, a "functional" molecule is a molecule in a form in which it exhibits a property by which it is characterized. By way of example, a functional enzyme is one which exhibits the characteristic catalytic activity by which the enzyme is characterized.

The term "greater uptake of a compound into a cell than the uptake of SL0101 into an otherwise identical cell" means that the compound has the ability to enter a cell at a greater rate than SL0101 or that more of said compound is taken up than SL0101. The term further encompasses the meaning that there can be greater levels of the compound, which can also be due to a lower rate of degradation or to a lower rate of efflux from the cell.

The term "inhibit," as used herein, refers to the ability of a compound of the invention to reduce or impede a described function. Preferably, inhibition is by at least 10%, more preferably by at least 25%, even more preferably by at least 50%, and most preferably, the function is inhibited by at least 75%.

The phrase "inhibit cancer cell growth", as used herein, refers to both direct and indirect inhibition of growth, regardless of the mechanism. For example, inhibiting a cancer cell from adhering to another cell or substrate can inhibit growth indirectly, when adhesion is required for the cell to proliferate.

The term "inhibit a protein", as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein, "inhibiting RSK" refers to the use of any compound, agent, or mechanism to inhibit RSK synthesis, levels, activity, or function are reduced or inhibited as described above.

As used herein, "an inhibitor of RSK" refers to any compound, agent, or mechanism whereby RSK synthesis, levels, activity, or function are reduced or inhibited as described above.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

As used herein, "modification" of a compound refers to a compound that's structure or composition has been somewhat changed from the original compound.

As used herein, the term "pharmaceutically acceptable carrier" includes any of the standard pharmaceutical carriers, such as a phosphate buffered saline solution, water and emulsions such as an oil/water or water/oil emulsion, and various types of wetting agents. As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" includes formulations for human and veterinary use.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and the like terms relate to the isolation of a molecule or compound in a form that is substantially free (at least 60% free, preferably 75% free, and most preferably 90% free) from other components normally associated with the molecule or compound in a native environment.

The term "regulate" refers to either stimulating or inhibiting a function or activity of interest.

As used herein, the use of the term "RSK" is intended to refer generically to all the human RSK isotypes, including RSK1, RSK2, RSK3, and RSK4. RSK1, RSK2, RSK3, and RSK4 are specific human isotypes that have previously been described in the literature.

The term "RSK activity", as used herein, includes synthesis, levels, activity, or function of RSK.

As used herein, the term "RSK inhibitor" includes any compound or condition that specifically inhibits or reduces the kinase activity of RSK or which inhibits any function of RSK. Such inhibitory effects may result from directly, or indirectly, interfering with the protein's ability to phosphorylate its substrate, or may result from inhibiting the expression (transcription and/or translation) of RSK.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

The term to "treat," as used herein, means reducing the frequency with which symptoms are experienced by a patient or subject or administering an agent or compound to reduce the frequency with which symptoms are experienced.

As used herein, "treating a disease or disorder" means reducing the frequency with which a symptom of the disease or disorder is experienced by a patient.

A "therapeutic" treatment is a treatment administered to a subject who exhibits signs of pathology, for the purpose of diminishing or eliminating those signs.

A "prophylactic" treatment is a treatment administered to a subject who does not exhibit signs of a disease or exhibits only early signs of the disease for the purpose of decreasing the risk of developing pathology associated with the disease.

Chemical Definitions

The general chemical terms used in the description of the compounds of the present invention have their usual meanings. For example, the term "alkyl" by itself or as part of another substituent means a straight or branched aliphatic chain having the stated number of carbon atoms.

The term "acyl" refers to alkylcarbonyl species and includes any group or radical of the form RCO—where R is an organic group. The term "acyl" further comprises an organic radical derived from an organic acid by removal of the hydroxyl group from the carboxyl group. The terms "acyl" and "OAc" are used interchangeably herein. The term "acylation" refers to the process of adding an acyl group to a compound.

The term butyryl as used herein encompasses its usual meaning in the art.

The term "halo" includes bromo, chloro, fluoro, and iodo.

The term "haloalkyl" as used herein refers to a alkyl radical bearing at least one halogen substituent, for example, chloromethyl, fluoroethyl or trifluoromethyl and the like.

The term "C1-Cn alkyl" wherein n is an integer, as used herein, refers to a branched or linear alkyl group having from one to the specified number of carbon atoms. Typically, C1-C6 alkyl groups include, but are not limited to, methyl, ethyl, n-propyl, iso-propyl, butyl, iso-butyl, sec-butyl, tert-butyl, pentyl, hexyl and the like.

The term "C2-Cn alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "C2-Cn alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

As used herein, the term "optionally substituted" refers to zero to four substituents, wherein the substituents are each independently selected. More preferredly, the term refers to zero to three independently selected substituents.

As used herein the term "aryl" refers to a mono- or bicyclic carbocyclic ring system having one or two aromatic rings including, but not limited to, phenyl, naphthyl, tetrahydronaphthyl, indanyl, indenyl, and the like. Aryl groups (including bicyclic aryl groups) can be unsubstituted or substituted with one, two, or three substituents independently selected from lower alkyl, haloalkyl, alkoxy, amino, alkylamino, dialkylamino, hydroxy, halo, and nitro. Substituted aryl includes aryl compounds having one or two C1-C6 alkyl, halo, or amino substituents. The term (alkyl)aryl refers to any aryl group which is attached to the parent moiety via the alkyl group.

The term "C3-Cn cycloalkyl" wherein n=4-8, represents cyclopropyl, cyclobutyl, cyclopentyl, cyclohexyl, cycloheptyl, and cyclooctyl.

The term "heterocyclic group" refers to a C3-C8 cycloalkyl group containing from one to three heteroatoms wherein the heteroatoms are selected from the group consisting of oxygen, sulfur, and nitrogen.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "lower alkyl" as used herein refers to branched or straight chain alkyl groups comprising one to eight carbon atoms, including methyl, ethyl, propyl, isopropyl, n-butyl, t-butyl, neopentyl and the like.

The term "heteroatom" means for example oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

The compounds of the present invention can contain one or more asymmetric centers in the molecule. In accordance with the present invention any structure that does not designate the stereochemistry is to be understood as embracing all the various optical isomers, as well as racemic mixtures thereof.

Compounds of the present invention that have one or more asymmetric carbon atoms may exist as the optically pure enantiomers, or optically pure diastereomers, as well as mixtures of enantiomers, mixtures of diastereomers, and racemic mixtures of such stereoisomers. The present invention includes within its scope all such isomers and mixtures thereof.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn, Ingold and Prelog, (Cahn et al. Angew. Chem. Inter. Edit., 5, 385; (1966) errata 511; Cahn et al. Angew. Chem., 78, 413; (1966) Cahn and Ingold J. Chem. Soc. (London), 612; (1951) Cahn et al. Experientia, 12, 81; (1956), Cahn, J. Chem. Educ., 41, 116, (1964)) or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of the present invention may exist in tautomeric forms and the invention includes both mixtures and separate individual tautomers. For example, the following structure:

is understood to represent a mixture of the structures:

as well as

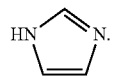

The terms 16:0, 18:0, 18:1, 20:4 or 22:6 hydrocarbon refers to a branched or straight alkyl or alkenyl group, wherein the first integer represents the total number of carbons in the group and the second integer represent the number of double bonds in the group.

The term, "parenteral" means not through the alimentary canal but by some other route such as subcutaneous, intramuscular, intraspinal, or intravenous.

Embodiments

Techniques not described herein which are useful for practicing the invention are available and known in the art (see Smith et al., U.S. patent application Ser. No. 10/517,328; Hecht et al., International Patent Publication WO 2006/

086103, published Aug. 17, 2006). Methods for adding acyl and butyryl groups to the core structure having formula I are described herein or are described in the art.

Techniques for preparing analogs, derivatives, and modifications of compounds such as 3Ac-SL0101 and Bu-SL0101 are known in the art or described herein. Some examples of diseases which may be treated according to the methods of the invention are discussed herein or would or known in the art.

In one aspect of the invention, the presently disclosed RSK inhibitors are used to treat various neoplastic diseases, including cancers such as prostate cancer, sarcoma, and breast cancer. Advantageously, since the inhibitors of the present invention inhibit RSK specifically in situ without toxic effects, the inhibitors can also be used as therapeutic interventions in non-terminal diseased states. One of ordinary skill in the art will appreciate that the compounds of the present invention can be administered in combination with other anti-tumor agents or therapeutic agents.

The term "neoplastic cells" as used herein relates to cells that constitute an abnormal new growth, i.e. cells that divide to form tissue that serves no physiological function in the host organism. As used herein, the term "tumor" refers to a mass or population of cells that result from excessive cell division and serve no physiological function in the host organism, whether malignant or benign. A "tumor" is further defined as two or more neoplastic cells. "Malignant tumors" are distinguished from benign growths or tumors in that, in addition to uncontrolled cellular proliferation, they will invade surrounding tissues and may additionally metastasize.

As used herein the term "neoplastic disease" relates to any disease that is characterized by the presence of neoplastic cells. Neoplastic diseases include cancer and other diseases characterized by the uncontrolled, abnormal growth of cells. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, kidney cancer, vulval cancer, thyroid cancer, hepatic carcinoma, skin cancer, melanoma, brain cancer, ovarian cancer, neuroblastoma, myeloma, various types of head and neck cancer, acute lymphoblastic leukemia, acute myeloid leukemia, Ewing sarcoma and peripheral neuroepithelioma. All of the possible cancers listed herein are included in, or may be excluded from, the present invention as individual species.

As used herein the term "anti-tumor agent" relates to agents known in the art that have been demonstrated to have utility for treating neoplastic disease. For example, antitumor agents include, but are not limited to, antibodies, toxins, chemotherapeutics, enzymes, cytokines, radionuclides, photodynamic agents, and angiogenesis inhibitors. Toxins include ricin A chain, mutant Pseudomonas exotoxins, diphtheria toxoid, streptonigrin, boamycin, saporin, gelonin, and pokeweed antiviral protein. Chemotherapeutics include 5-fluorouracil (5-FU), daunorubicin, cisplatinum, bleomycin, melphalan, taxol, tamoxifen, mitomycin-C, and methotrexate as well as any of the compounds described in U.S. Pat. No. 6,372,719 (the disclosure of which is incorporated herein by reference) as being chemotherapeutic agents. Radionuclides include radiometals. Photodynamic agents include porphyrins and their derivatives.

Angiogenesis inhibitors are known in the art and include natural and synthetic biomolecules such as paclitaxel, O-(chloroacetyl-carbomyl) fumagillol ("TNP-470" or "AGM 1470"), thrombospondin-1, thrombospondin-2, angiostatin, human chondrocyte-derived inhibitor of angiogenesis ("hCHIAMP"), cartilage-derived angiogenic inhibitor, platelet factor-4, gro-beta, human interferon-inducible protein 10 ("IP10"), interleukin 12, Ro 318220, tricyclodecan-9-yl xanthate ("D609"), irsogladine, 8,9-dihydroxy-7-methyl-benzo[b]quinolizinium bromide ("GPA 1734"), medroxyprogesterone, a combination of heparin and cortisone, glucosidase inhibitors, genistein, thalidomide, diamino-antraquinone, herbimycin, ursolic acid, and oleanolic acid. Anti-tumor therapy includes the administration of an anti-tumor agent or other therapy, such as radiation treatments, that has been reported as being useful for treating cancer.

The purified flavonoid compounds and RSK specific inhibitory compounds of the present invention can be combined with pharmaceutically acceptable carriers, stabilizing agents, solubilizing agents, and fillers known to those skilled in the art to prepare pharmaceuticals for administration to warm blooded vertebrates. One of ordinary skill in the art will appreciate that even though a compound may have high specificity for inhibiting RSK activity or function, the compound may have other activities as well. The compositions can be formulated using standard delivery vehicles and standard formulations for oral, parenteral, inhalation or transdermal delivery. Such pharmaceuticals have use in treating neoplastic disease, neurological diseased states (such as epilepsy) or other disease states characterized by inappropriate RSK activity.

In accordance with one embodiment of the invention a RSK specific inhibitory compound or composition (i.e. a RSK specific inhibitory extract, or specific flavonoid compound), is combined with one or more antitumor agents, including those selected from the group consisting of antibodies, toxins, chemotherapeutics, enzymes, cytokines, radionuclides, photodynamic agents, and angiogenesis inhibitors to prepare a pharmaceutical composition. Toxins include ricin A chain, mutant Pseudomonas exotoxins, diphtheria toxoid, streptonigrin, boamycin, saporin, gelonin, and pokeweed antiviral protein. Chemotherapeutics include 5-fluorouracil (5-FU), daunorubicin, cisplatinum, bleomycin, melphalan, taxol, tamoxifen, mitomycin-C, and methotrexate. Radionuclides include radiometals. Photodynamic agents include porphyrins and their derivatives. Angiogenesis inhibitors are known in the art and include natural and synthetic biomolecules such as paclitaxel, O-(chloroacetyl-carbomyl) fumagillol ("TNP-470" or "AGM 1470"), thrombospondin-1, thrombospondin-2, angiostatin, human chondrocyte-derived inhibitor of angiogenesis ("hCHIAMP"), cartilage-derived angiogenic inhibitor, platelet factor-4, gro-beta, human interferon-inducible protein 10 ("IP10"), interleukin 12, Ro 318220, tricyclodecan-9-yl xanthate ("D609"), irsogladine, 8,9-dihydroxy-7-methyl-benzo[b]quinolizinium bromide ("GPA 1734"), medroxyprogesterone, a combination of heparin and cortisone, glucosidase inhibitors, genistein, thalidomide, diamino-antraquinone, herbimycin, ursolic acid, and oleanolic acid.

The RSK inhibitors of the present invention have been shown to inhibit proliferation of a transformed cell without substantially altering the proliferation rate of non-transformed cell growth. Therefore, the inhibitors of the present invention are not toxic to non-transformed cells.

Processes for preparing compounds of formula I, or analogs, derivatives, or modifications thereof, or for preparing intermediates useful for preparing compounds of formula I are provided as further embodiments of the invention. Intermediates useful for preparing compounds of formula I are also provided as further embodiments of the invention.

SL0101 is a kaempferol, and kaempferol has the structure:

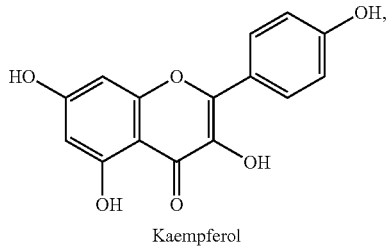 [SMILES: O=c1c(O)c(-c2ccc(O)cc2)oc2cc(O)cc(O)c12]

Kaempferol while SL0101 has the structure:

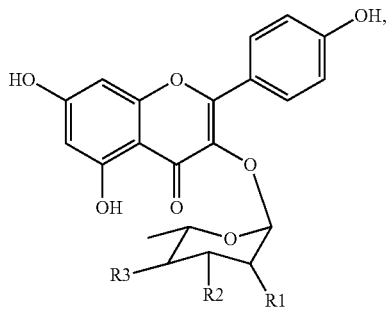

wherein R1 is OH and R2 and R3 are each OAc (Xu et al., 2006, Biorg. Med. Chem., 14:3974-3977) (also see FIG. 1 herein). Two of the lead compounds of the present invention, 3Ac-SL0101 and Bu-SL0101, have been modified on the rhamnose moiety of SL0101, however, the invention further encompasses modification of the kaempferol structure wherein said modification does not appreciably affect the biologic activity of the compound as to its ability to inhibit cell proliferation or to inhibit excessive Rsk activity. Therefore, in one embodiment, the present invention encompasses not only a derivative of formula I, wherein R1, R2 and R3 comprise OAc and butyryl, it further encompasses the preparation and use of compounds wherein the kaempferol core structure is modified without affecting the desired activity described herein.

The present invention further comprises compounds which have been modified to include greater stability of interactions between SL0101 and RSK and to have greater efficacy than SL0101. In one aspect, this is accomplished by replacing the hydroxyl groups of the flavonoid with sulfhydryls. In another aspect, this is accomplished by replacing the hydroxyl groups of the sugar with acetamide, or derivatives of acetamide. To that end, the present invention further provides a compound having the structure of formula II:

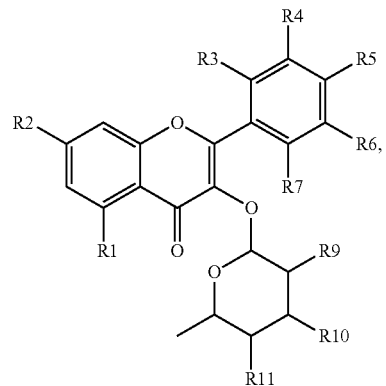

wherein $R_1$, $R_2$, $R_3$, $R_4$, $R_5$, $R_6$, and $R_7$ are independently selected from the group consisting of OH, —OCOR$_8$, —COR$_8$, —SR$_8$, and $C_1$-$C_4$ alkoxy;

$R_8$ is H or $C_1$-$C_4$ alkyl; and $R_9$, $R_{10}$ and $R_{11}$ are independently selected from the group consisting of H, OH, —OCOR$_8$, —COR$_8$, —NHOCOR$_8$ and $C_1$-$C_4$ alkoxy.

The compounds of formula II may also include acyl and butyryl groups as described for the compounds of formula I.

The compounds comprised by formula II encompass replacing the hydroxyl groups of the flavonoid with sulfhydryls (—SH).

The compounds comprised by formula II further encompass replacing the hydroxyl groups on the sugar with an acetamide (NHOCOH). For example:

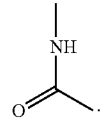

The acetamide can be a substituted acetamide comprising NHOCOR$_8$ as indicated above for the generic structure of formula II.

Based on the information provided herein and on what is known in the art, one of ordinary skill in the art will be able to prepare the compounds of formulas I and II and to test the compounds for their desired activity.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Processes for preparing compounds of formula I and formula II are provided as further embodiments of the invention and are illustrated by the following procedures in which the meanings of the generic radicals are as given above unless otherwise qualified.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, -ketoglutarate, and -glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion.

Alkali metal (for example, sodium, potassium or lithium) or alkaline earth metal (for example calcium) salts of carboxylic acids can also be made.

The compounds of formula I and formula II can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formulas I and II to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formulas I and II can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formulas I and II in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The present invention further encompasses administration of combinations of at least one compound of formula I and at least one compound of formula II. The present invention further encompasses administration of at least one compound of formula I and/or formula II and at least one additional therapeutic agent such as an anti-tumor agent, anti-angiogenic agent, or other agent.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

The method of the invention includes a kit comprising an inhibitor identified in the invention and an instructional material which describes administering the inhibitor or a composition comprising the inhibitor to a cell or a subject. This should be construed to include other embodiments of kits that are known to those skilled in the art, such as a kit comprising a (preferably sterile) solvent suitable for dissolving or suspending the composition of the invention prior to administering the compound to a cell or a subject. Preferably the subject is a human.

In accordance with the present invention, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the compounds of the present invention. Therefore, the examples should be construed to encompass any and all variations which become evident as a result of the teaching provided herein.

EXAMPLES

Methods

Kinase Assays

Glutathione-S-transferase (GST)-fusion protein (1 µg) containing the sequence—RRRLASTNDKG (for serine/threonine kinase assays) was adsorbed in the wells of LumiNunc 96-well polystyrene plates (MaxiSorp surface treatment). The wells were blocked with sterile 3% tryptone in phosphate buffered saline. Kinase (5 nM) in 70 µL of kinase buffer (5 mM β-glycerophosphate pH 7.4, 25 mM HEPES, pH 7.4, 1.5 mM DTT, 30 mM $MgCl_2$, 0.15 M NaCl) was dispensed into each well. Compound at indicated concentrations or vehicle was added and reactions were initiated by the addition of 30 µL of ATP to a final ATP concentration of 10 µM. Reactions were terminated after 30 min by addition of 75 µL of 500 mM EDTA, pH 7.5. All assays measured the initial velocity of reaction. After extensive washing of wells, anti-p-p140 antibody, a polyclonal phosphospecific antibody developed against the phosphopeptide, CGLA(pS)TND, and HRP-conjugated anti-rabbit antibody (211-035-109, Jackson ImmunoResearch Laboratories, West Grove, Pa.) were used to detect serine phosphorylation of the substrate. HRP activity was measured using Western Lightning Chemiluminescence Reagent (NEL102, PerkinElmer Life Sciences) according to the manufacturer's protocol. Maximum and minimum activity is the relative luminescence detected in the presence of vehicle and 200 mM EDTA, respectively. His-tagged active RSK was expressed in Sf9 cells and purified using NiNTA resin (Qiagen, Valencia, Calif.). Baculovirus was prepared using the Bac-to-Bac® baculovirus expression system (Invitrogen, Carlsbad, Calif.). Maximum responses and the concentrations at half the inhibitory response ($IC_{50}$) were determined by performing a best-fit analysis of the data (GraphPad Prism).

Cell Culture

For proliferation studies cells were seeded at 5000 cells per well in 96 well tissue culture plates in the appropriate medium as described by American Type Culture Collection. After 24 hours, the medium was replaced with medium containing compound or vehicle as indicated. Cell viability was measured at indicated time points using CellTiter-Glo™ assay reagent (Promega, Madison, Wis.) according to manufacturer's protocol. Maximum responses and the concentrations of half the effective response ($EC_{50}$) were determined by performing a best-fit analysis of the data (GraphPad Prism). For specificity studies, cells were seeded at $3 \times 10^5$ cells/well in 6 well plates. After 24 hours, the cells were serum-starved for 24 hours then incubated with compound or vehicle for 4 hours prior to a 20 minute treatment with PDB. Cells were lysed with boiling SDS-sample buffer without dithiothreitol (DTT). The lysates were normalized for total protein, and DTT was added to an aliquot, which was electrophoresed and immunoblotted. Antibodies used on cell lysates included anti-pan-MAPK (anti-ERK1/2) (610124) from BD Transduction Laboratories; anti-phospho-MAPK (V8031) from Promega; anti-eEF2 (2332), anti-phospho-eEF2 (2331), anti-phospho-Akt Substrate (9611), anti-phospho-PKA Substrate (9621), and anti-phospho-PKC Substrate (2261) from Cell Signaling Technology. Anti-Ran was a generous gift from Ian Macara (University of Virginia).

Chemistry

Reagents and solvents were reagent grade and used without further purification. Methylene chloride was distilled from calcium hydride. Anhydrous grade THF was purchased from VWR. All reactions involving air or moisture sensitive reagents or intermediates were performed under a nitrogen or argon atmosphere. Flash chromatography was performed using Silicycle 40-60 mesh silica gel. Analytical TLC was performed using 0.25 mm EM silica gel 60 $F_{250}$ plates that were visualized by irradiation (254 nm) or by staining with Hanessian's stain (cerium molybdate). Optical rotations were obtained using a Jasco digital polarimeter. $^1H$ and $^{13}C$ NMR spectra were obtained using 300 MHz and 500 MHz Varian instruments. Chemical shifts are reported in parts per million (ppm δ) referenced to the residual $^1H$ resonance of the solvent (CDCl$_3$, 7.26 ppm; DMSO-d$_6$, 2.49 ppm). $^{13}C$ spectra were referenced to the residual $^{13}C$ resonance of the solvent (CDCl$_3$, 77.3 ppm; DMSO-d$_6$, 39.5 ppm). Splitting patterns are designated as follows: s, singlet; br, broad; d, doublet; dd, doublet of doublets; t, triplet; q, quartet; m, multiplet. High resolution mass spectra were obtained at the Michigan State University-NIH Mass Spectrometry Facility. LogP values were calculated using Molinspiration Property Calculation Service (see their website).

Phenyl 3,4-Di-O-butyryl-2-O-benzyl-1-thio-α-L-rhamnopyranoside (2)

A solution containing 0.87 g (2.51 mmol) of phenyl 2-O-benzyl-1-thio-α-L-rhamnopyranoside (1)[11], 1.19 g (1.25 mL, 7.54 mmol) of butyric anhydride, 1.01 g (1.37 mL, 10.0 mmol) of NEt$_3$, and 0.03 g (0.25 mmol) of 4-N,N-dimethylaminopyridine in 10 mL of anhydrous CH$_2$Cl$_2$ was stirred at room temperature under a N$_2$ atmosphere for 2 h. The reaction mixture was then diluted with 100 mL of CH$_2$Cl$_2$ and washed with two 100-mL portions of H$_2$O. The organic layer was separated, dried (MgSO$_4$) and concentrated under diminished pressure. The residue was purified by flash chromatography on a silica gel column (25×4 cm). Elution with 3:1 hexanes-ethyl acetate gave 2 as a colorless oil: yield 1.21 g (100%); silica gel TLC R$_f$ 0.40 (6:1 hexanes-ethyl acetate); $[α]^{21}_D$-50.1 (c 1.0, CHCl$_3$); $^1H$ NMR (CDCl$_3$) δ 0.95 (q, 6H, J=7.5 Hz), 1.24 (d, 3H, J=6.3 Hz), 1.64 (m, 4H), 2.26 (m, 4H), 4.11 (dd, 1H, J=3.3 and 1.8 Hz), 4.30 (m, 1H), 4.55 (d, 1H, J=12.3 Hz), 4.68 (d, 1H, J=12.3 Hz), 5.20 (dd, 1H, J=9.9 and 3.0 Hz), 5.32 (t, 1H, J=9.9 Hz), 5.51 (d, 1H, J=1.5 Hz), 7.31 (m, 8H) and 7.45 (m, 2H); $^{13}C$ NMR (CDCl$_3$) δ 13.90, 17.72, 18.54, 18.70, 36.28, 36.41, 68.16, 71.31, 71.42, 72.80, 85.68, 127.69, 128.13, 128.64, 129.34, 131.55, 134.39, 137.67, 172.70 and 173.06; mass spectrum (FAB), m/z 487.2155 (M+H)$^+$ (C$_{27}$H$_{35}$O$_6$S requires 487.2154).

3,4-Di-O-butyryl-2-O-benzyl-α-L-rhamnopyranosyl Bromide (3)

To a solution containing 0.54 g (1.12 mmol) of 2 in 5 mL of anhydrous CH$_2$Cl$_2$ at 0° C. under argon was added 0.21 g (0.07 mL, 1.34 mmol) of Br$_2$. The reaction mixture was stirred at 0° C. for 20 min then diluted with 20 mL of CH$_2$Cl$_2$ and washed with 3% aq NaHSO$_3$. The organic layer was separated, dried (MgSO$_4$) and concentrated under diminished pressure. The crude residue was then purified by flash chromatography on a silica gel column (26×4 cm). Elution with 2:1 hexanes-ethyl acetate gave 3 as a colorless oil: yield 0.49 g (96%); silica gel TLC R$_f$ 0.21 (2:1 hexanes-ethyl acetate); $^1H$ NMR (CDCl$_3$) δ 0.94 (q, 6H, J=7.5 Hz), 1.25 (d, 3H, J=6.3 Hz), 1.62 (m, 4H), 2.23 (m, 4H), 4.04 (m, 1H), 4.11 (dd, 1H, J=3.3 and 1.8 Hz), 4.64 (q, 2H, J=12.3 Hz), 5.30 (t, 1H, J=9.9 Hz), 5.57 (dd, 1H, J=10.2 and 3.3 Hz), 6.34 (d, 1H, J=0.6 Hz) and 7.33 (m, 5H); $^{13}C$ NMR (CDCl$_3$) δ 13.71, 17.11, 18.31, 18.47, 35.99, 36.11, 69.67, 70.27, 71.26, 73.37, 79.20, 86.35, 127.96, 128.18, 128.57, 137.18, 172.31 and 172.68. Note: this compound must be used promptly; product decomposes rather rapidly (1-2 days).

Kaempferol 3-O-(3",4"-di-O-butyryl-α-L-rhamnopyranoside) (Bu-SL0101) (5)

To a stirred suspension containing 0.13 g (0.23 mmol) of 4,[11] 0.11 g (0.46 mmol) of Ag$_2$O and 4 Å molecular sieves in 5 mL CH$_2$Cl$_2$ was added 0.21 g (0.46 mmol) of 3 as a solution in 4 mL of CH$_2$Cl$_2$. The reaction mixture was stirred at room temperature for 4 h, then diluted with 20 mL of CH$_2$Cl$_2$ and filtered through a Celite pad. The filtrate was concentrated under diminished pressure. This crude residue was then dissolved in 5 mL of 1:1 THF-MeOH and 45 mg of Pd(OH)$_2$/C was added. The reaction vessel was purged with H$_2$ three times then maintained under H$_2$ atmosphere for 2 h. The reaction mixture was then filtered through Celite and the filtrate was concentrated. The residue was purified by flash chromatography on a silica gel column (25×2 cm). Elution with 1:1:0.1 hexanes-ethyl acetate-methanol gave 5 as a brown solid: yield 0.090 g (69%); silica gel TLC R$_f$ 0.30 (1:1:0.1 hexanes-ethyl acetate-methanol); $[α]^{20}_D$-115.6 (c 1.2, CHCl$_3$); $^1H$ NMR (DMSO-d$_6$) δ 0.85 (d, 3H, J=6.3 Hz), 0.97 (m, 6H), 1.64 (m, 4H), 2.33 (m, 4H), 3.49 (m, 1H), 4.46 (s, 1H), 4.79 (br s, 1H); 5.14 (t, 1H, J=9.9 Hz), 5.27 (dd, 1H, J=6.3 and 3.0 Hz), 5.66 (d, 1H, J=1.8 Hz), 6.32 (d, 1H, J=1.8 Hz), 6.53 (d, 1H, J=2.1 Hz), 7.11 (d, 2H, J=8.7 Hz), 7.92 (d, 2H, J=8.4 Hz), 9.39 (br s, 2H) and 12.68 (s, 1H); mass spectrum (FAB), m/z 573.1970 (M+H)$^+$ (C$_{29}$H$_{33}$O$_{12}$ requires 573.1972).

5,7-Bis-(benzoxy)-2-(4-(benzoxy)phenyl)-3-[2",3",4"-tri-O-acetyl-α-L-rhamnopyranosyloxy]-4H-chromen-4-one (7)

To a stirred suspension containing 0.090 g (0.162 mmol) of 4,[11] 0.075 g (0.324 mmol) of Ag$_2$O and 4 Å molecular sieves in 5 mL CH$_2$Cl$_2$ was added 0.114 g (0.324 mmol) of 6[12] as a solution in 4 mL of CH$_2$Cl$_2$. The reaction mixture was stirred at room temperature for 24 hours under N$_2$ then diluted with 20 mL of CH$_2$Cl$_2$ and filtered through a Celite pad. The filtrate was concentrated under diminished pressure. The residue was purified by flash chromatography on a silica gel column (20×3 cm). Elution with 2:1 hexanes-ethyl acetate gave 7 as a light yellow foam: yield 0.125 g (93%); silica gel TLC R$_f$ 0.41 (2:1 hexanes-ethyl acetate); $[α]^{22}_D$-96.8 (c 0.5, CHCl$_3$); $^1H$ NMR (CDCl$_3$) δ 0.85 (d, 3H, J=6.3 Hz), 1.97 (s, 3H), 2.00 (s, 3H), 2.11 (s, 3H), 3.39 (m, 1H), 4.94 (t, 1H, J=9.9 Hz), 5.07 (s, 2H), 5.15 (s, 2H), 5.30 (s, 2H), 5.34 (m, 1H), 5.74 (s, 2H), 6.45 (d, 1H, J=1.8 Hz), 6.55 (d, 1H, J=1.8 Hz), 7.16 (d, 2H, J=8.7 Hz), 7.39 (m, 13H), 7.57 (d, 2H, J=7.5 Hz) and 7.87 (d, 2H, J=8.7 Hz); $^{13}C$ NMR (CDCl$_3$) δ 17.00, 20.69, 20.83, 67.99, 68.98, 69.18, 70.05, 70.40, 70.57, 70.67, 93.86, 97.79, 98.23, 109.89, 114.81, 122.97, 126.54, 127.30, 127.51, 127.61, 128.13, 128.36, 128.60, 128.68, 130.33, 135.54, 136.22, 136.27, 136.41, 154.16, 158.75, 159.74, 160.49, 162.78, 169.52, 169.80, 169.88 and 172.82; mass spectrum (FAB), m/z 829.2865 (M+H)$^+$ (C$_{48}$H$_{45}$O$_{13}$ requires 829.2860).

Kaempferol 3-O-(2",3",4"-tri-O-acetyl-α-L-rhamnopyranoside) (3Ac-SL0101) (8)

A stirred suspension containing 0.100 g (0.121 mmol) of 7 and 0.040 g of Pd(OH)$_2$ in 5 mL of 1:1 THF-MeOH was purged with $H_2$ three times then allowed to maintain under $H_2$ (balloon pressure) for 1.5 hours. The reaction was then filtered through Celite and the filtrate was concentrated. The residue was purified by flash chromatography on a silica gel column (20×2 cm). Elution with 1:1:0.1 hexanes-ethyl acetate-methanol gave 8 as a yellow foam: yield 0.064 g (95%); silica gel TLC $R_f$ 0.37 (1:1:0.1 hexanes-ethyl acetate-methanol); $[\alpha]^{22}_D$ -92.2 (c 0.6, $CHCl_3$); $^1H$ NMR ($CDCl_3$) δ 0.92 (t, 3H, J=6.3 Hz), 2.01 (s, 3H), 2.02 (s, 3H), 2.05 (s, 3H), 3.52 (m, 1H), 4.96 (t, 1H, J=9.9 Hz), 5.33 (dd, 1H, J=9.9 and 3.0 Hz), 5.30 (s, 1H), 5.63 (s, 1H), 6.25 (s, 1H), 6.35 (s, 1H), 6.99 (d, 2H, J=8.1 Hz), 7.18 (br s, 1H), 7.72 (d, 2H, J=8.1 Hz), 7.89 (br s, 1H) and 12.49 (s, 1H); $^{13}C$ NMR ($CDCl_3$) δ 16.97, 20.68, 20.74, 20.78, 68.33, 69.26, 70.38, 77.20, 94.18, 98.08, 99.27, 105.27, 115.66, 121.53, 130.67, 133.80, 156.78, 157.64, 159.10, 161.66, 163.08, 170.47, 170.57, 171.08 and 177.69; mass spectrum (FAB), m/z 559.1449 $(M+H)^+$ ($C_{27}H_{27}O_{13}$ requires 559.1452).

Results

Rhamnose Acylation is Critical for Inhibition of MCF-7 Cell Growth

Figure 2A:
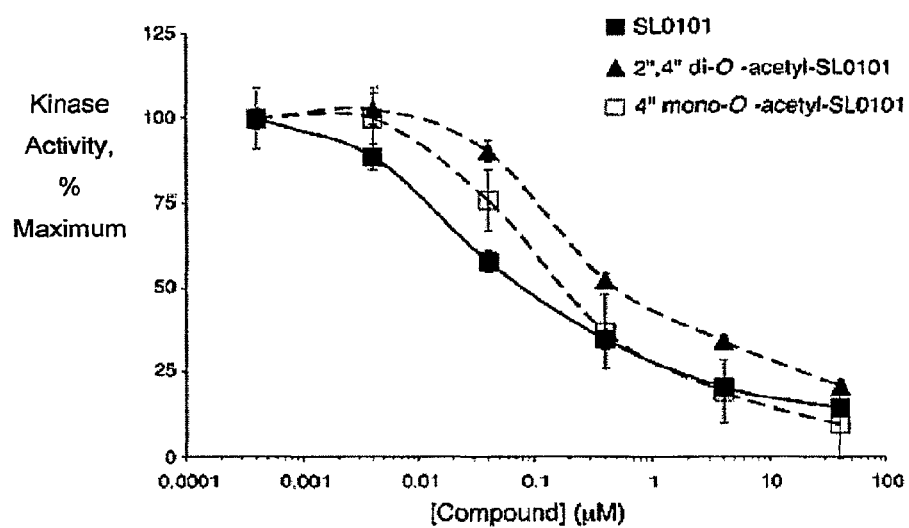
FIG. 2, comprising FIGS. 2A and 2B, graphically illustrates the effect of SL0101, 2",4"-di-O-acetyl-SL0101 and 4"-mono-O-acetyl-SL0101 on RSK activity. (2A) The potency of purified compounds in inhibiting RSK catalytic activity in vitro was measured. Kinase assays were performed using immobilized substrate. The reactions were initiated by the addition of 10 μM ATP (final concentration). Reactions were terminated after 30 min. All assays measured the initial reaction velocity. The extent of phosphorylation was determined using phosphospecific antibodies in combination with HRP-conjugated secondary antibodies. HRP activity was measured as described in the Experimental. Maximum and minimum activity is the relative luminescence detected in the presence of vehicle and 200 mM EDTA, respectively. Points, mean (n=2 in triplicate); bars=SD. (2B) The potency of purified compounds as inhibitors of MCF-7 cell proliferation was determined. MCF-7 cells were treated with vehicle or 50 μM SL0101, 2",4" di-O-acetyl-SL0101, or 4" mono-O-acetyl-SL0101 and cell viability was measured after 72 h of treatment. Values given are the fold proliferation. Points, mean (n=3 in quadruplicate); bars=SD.

To investigate the possibility of improving the potency of SL0101, two compounds structurally related to SL0101 were prepared and characterized for their ability to inhibit RSK activity. These compounds, kaempferol 3-O-(2",4"-di-O-acetyl-α-L-rhamnopyranoside), (2",4"-di-O-acetyl-SL0101), and kaempferol 3-O-(4"-mono-O-acetyl-α-L-rhamnopyranoside), (4"-mono-O-acetyl-SL0101), differ from SL0101 in either the position or number of acetyl groups present on the rhamnose moiety (FIG. 1) and were obtained during the purification of SL0101 from F. refracta. The ability of the purified compounds to inhibit RSK activity was determined in an in vitro kinase assay using recombinant, constitutively active RSK2.[4] The data were fit using non-linear regression analysis and the $IC_{50}$ values for 4"-mono-O-acetyl-SL0101 and 2",4"-di-O-acetyl-SL0101 were ~140 nM and ~260 nM, respectively (FIG. 2A), which is similar to the $IC_{50}$ of ~50-100 nM obtained for SL0101. Thus all three related compounds are able to inhibit RSK catalytic activity in vitro, which is in agreement with the observations reported by Maloney and Hecht.[11]

Figure 2B:
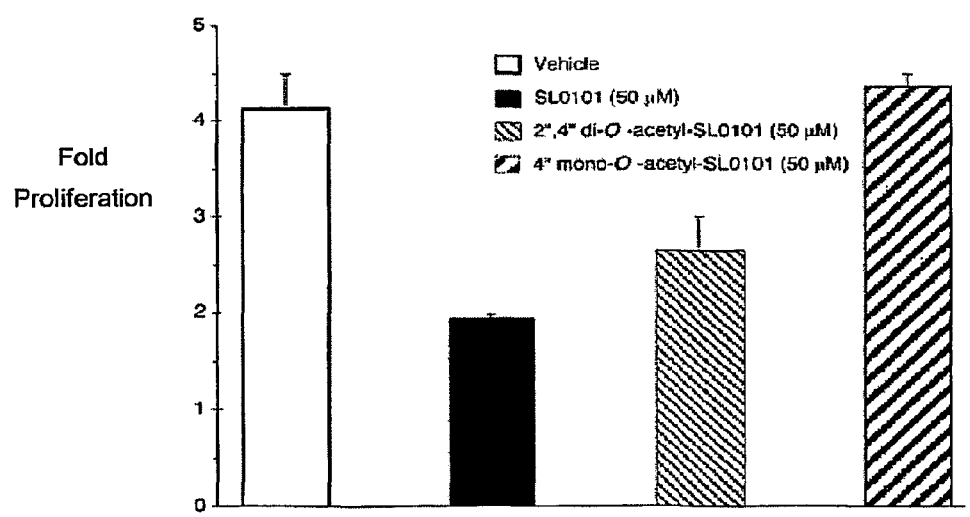

To determine whether the related compounds inhibit RSK activity in intact cells we examined their ability to inhibit the proliferation of MCF-7 cells. Previously we showed that SL0101 inhibits MCF-7 cell proliferation by specifically inhibiting RSK activity.[4] SL0101 inhibited MCF-7 cell proliferation with an $EC_{50}$ of ~50 μM,[4] and the current results are in agreement with those observations (FIG. 2B). SL0101 and 2",4"-di-O-acetyl-SL0101 at 50 μM were similarly effective at inhibiting MCF-7 cell growth. However, 4" mono-O-acetyl-SL0101 did not inhibit MCF-7 cell proliferation at 50 μM. These data show that the position of the acetyl groups was not critically important in determining the in vitro affinity for RSK. However, only the compounds with two acetyl groups inhibited RSK activity in intact cells. It is likely that the acetyl groups facilitate effective uptake of the inhibitors into the cell.

Based on the results disclosed herein, it was reasoned that increasing the cellular uptake of SL0101 by enhancing its hydrophobic, character might afford a more potent RSK inhibitor in intact cells. To test this hypothesis kaempferol 3-O-(3",4"-di-O-butyryl-α-L-rhamnopyranoside) (Bu-SL0101) and kaempferol 3-O-(2",3",4"-tri-O-acetyl-α-L-rhamnopyranoside) (3Ac-SL0101) were synthesized. The calculated LogPs of Bu-SL0101 and 3Ac-SL0101 are 4.30 and 3.07, respectively, compared to 2.56 for SL0101.

Synthesis of SL0101 Analogs

The syntheses of both Bu-SL0101 (5) and 3Ac-SL0101 (8) utilized methodology and intermediates described in the previously reported synthesis of SL0101.[11] Accordingly, bis-esterification of phenyl 2-O-benzyl-1-thio-α-L-rhamnopyranoside (1) was achieved using butyric anhydride, $NEt_3$ and catalytic DMAP in quantitative yield to afford phenylthioglycoside 2 (Scheme 1). Bromination of the anomeric position using elemental bromine at 0° C. gave glycosyl bromide 3 in 96% yield. Glycosylation of flavonol 4 with 3 was carried out using heterogenous activation conditions ($Ag_2O$). Preparation of 4 was achieved in three steps from commercially available 4',5,7-trihydroxyflavanone (naringenin) as described previously.[11] The crude, fully protected Bu-SL0101 was debenzylated by hydrogenolysis (Pd(OH)$_2$, $H_2$) to afford Bu-SL0101 (5) in 69% yield for two steps. The synthesis of 3Ac-SL0101 was carried out in a similar manner except that 1-bromo-2,3,4-tri-O-acetyl-α-L-rhamnose (6) was used in the glycosylation reaction with 4. Glycosyl bromide 6 was prepared using a method reported by Morillo and coworkers in two steps from L-rhamnose.[12] Subsequent coupling of 4 with 6 gave the desired perbenzylated 3Ac-SL0101 (7) in 93% yield, exclusively as the α-anomer. Complete debenzylation proceeded smoothly using Pd(OH)$_2$ to afford 3Ac-SL0101 (8) in 95% yield.

Bu-SL0101 and 3Ac-SL0101 Inhibit RSK Activity In Vitro and in the Intact Cell

Figure 3A:
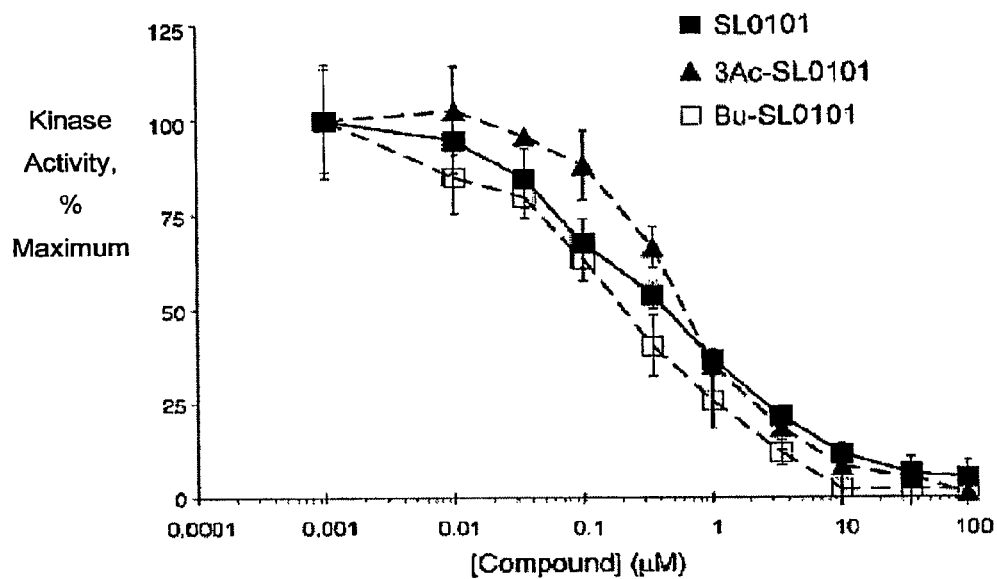
FIG. 3, comprising FIGS. 3A and 3B, demonstrates the inhibition of RSK activity by Bu-SL0101 and 3Ac-SL0101. (3A) The potency of the synthesized compounds in inhibiting RSK catalytic activity in vitro was measured as described in FIG. 2A and is graphically illustrated. (3B) Represents an images of immunoblots where serum-deprived MCF-7 cells were pre-incubated with vehicle, or the indicated concentration of inhibitor for 4 h. Cells were treated with 500 nM PDB or vehicle for 20 min prior to lysis. Protein concentration of lysates was measured and lysates were electrophoresed, transferred and immunoblotted. Equal loading of lysate is demonstrated by the anti-eEF2 and anti-ERK1/2 immunoblots.

The ability of the analogs to inhibit RSK activity was determined in an in vitro kinase assay and compared to the results obtained with synthesized SL0101.[11] The data were fit using non-linear regression analysis and the $IC_{50}$s for Bu-SL0101 and 3Ac-SL0101 were 212 nM and 580 nM, respectively, as compared to 370 nM obtained for the synthesized SL0101 (FIG. 3A). For reasons that are not clear, we consistently obtain an $IC_{50}$ for the synthesized SL0101 that is higher than that of the material originally isolated from F. refracta. Nonetheless, as discussed above, kaempferol rhamnopyranosides with varying numbers and positions of acetyl groups on the rhamnose moiety inhibited RSK activity in the in vitro kinase assay with similar $IC_{50}$s. In agreement with these data, the addition of a third acetyl group, generating 3Ac-SL0101, did not substantially alter the in vitro $IC_{50}$. Furthermore, replacement of the acetyl groups on the rhamnose with butyryl groups also did not appreciably influence the in vitro $IC_{50}$.

Figure 3B:
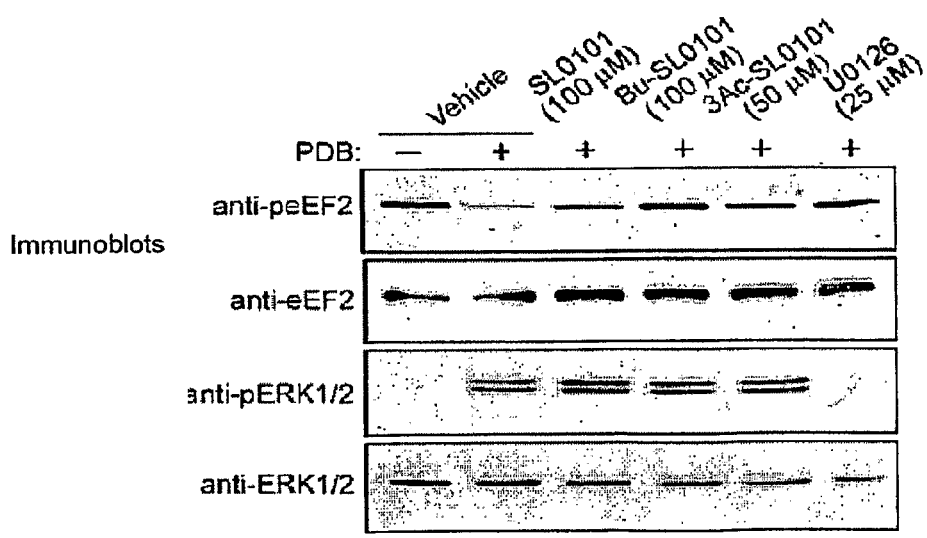

To determine whether 3Ac-SL0101 and Bu-SL0101 inhibited RSK in intact cells we examined the phosphorylation of eukaryotic elongation factor 2 (eEF2) in MCF-7 cells. eEF2 mediates the translocation step in mRNA translation. eEF2 activity is regulated by phosphorylation and it is inactivated by a highly specific kinase, EF2 kinase (EF2K). RSK phosphorylates and inactivates EF2K in response to mitogenic stimulation, which leads to a decrease in phosphorylation of eEF2.[13] Thus, under conditions such as serum deprivation, which leads to low RSK activity, eEF2 is phosphorylated by the active EF2K. However, stimulation of RSK activity by mitogens results in reduced phosphorylation of eEF2 due to inactivation of EF2K by RSK. Therefore, the phosphorylation state of eEF2 during mitogenic stimulation is an indicator of RSK activity. Treatment of MCF-7 cells with the mitogen phorbol dibutyrate (PDB) inactivated EF2K as shown by the reduced levels of phosphorylated eEF2 (FIG. 3B, compare lanes 1 and 2). The levels of total eEF2 were not altered by PDB treatment as shown by the anti-eEF2 immunoblot. However, pre-incubation of cells with SL0101 or its analogs eliminated PDB-mediated inactivation of eEF2K as shown by the elevated levels of phosphorylated eEF2 (FIG. 3B, cf lanes 3-5 with lane 2). In agreement with the literature, the levels of eEF2 phosphorylation also remained increased in the presence of U0126.[13] We have previously demonstrated that SL0101 does not affect the activation of MAPK, as detected by the anti-active MAPK antibody.[4] Here we show that neither 3Ac-SL0101 nor Bu-SL0101 alter PDB-stimulated MAPK activation (FIG. 3B). Therefore, Bu-SL0101 and 3Ac-SL0101, like SL0101, do not inhibit upstream kinases necessary for PDB-induced MAPK activation, namely MEK, Raf and protein kinase C (PKC).

3Ac-SL0101 is a Specific RSK Inhibitor

Figure 4:
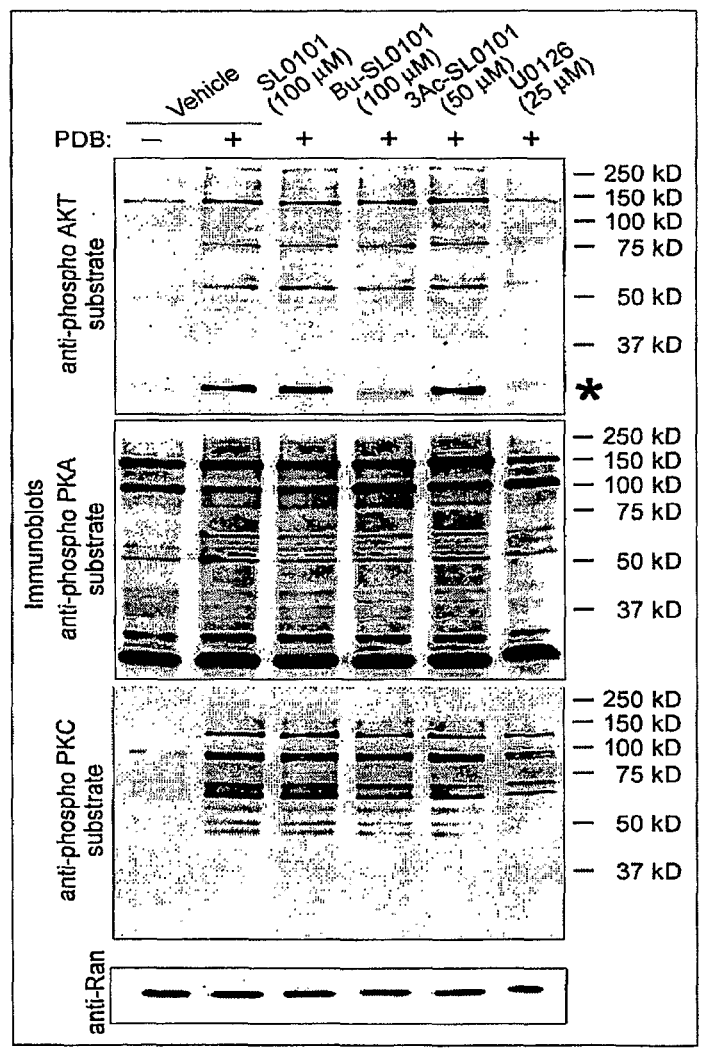
FIG. 4 represents images of immunoblots illustrating a comparison of the effect of Bu-SL0101, 3Ac-SL0101 and SL0101 on phosphorylation patterns in intact cells. MCF-7 cell lysates normalized for protein concentration were electrophoresed, transferred and immunoblotted with anti-phospho-PKA substrate, anti-phospho-PKC substrate or anti-phospho-AKT substrate. Equal loading of lysate is demonstrated by the anti-Ran immunoblot. The asterisk indicates the location of a protein whose PDB-induced phosphorylation is inhibited by pre-treatment with U0126 or Bu-SL0101.

To determine whether 3Ac-SL0101 and Bu-SL0101 demonstrated the same specificity as SL0101 in intact cells the phosphorylation patterns from MCF-7 cells pre-incubated with SL0101 or its analogs prior to stimulation with PDB were compared. The lysates were immunoblotted with multiple phospho-specific substrate antibodies. We have previously shown that SL0101 does not alter the phosphorylation patterns detected by these antibodies whereas changes are readily detected in cells treated with U0126, as well as protein kinase A (PKA) or PKC inhibitors.[4] The phosphorylation patterns from PDB-treated cells pre-incubated with vehicle, 3Ac-SL0101 or SL0101 were similar (FIG. 4). But unlike 3Ac-SL0101 and SL0101, pre-treatment with Bu-SL0101 decreased the PDB-induced phosphorylation of a ~25 kDa protein, as detected by the anti-phospho AKT substrate antibody. These results show that Bu-SL0101 is not specific for inhibition of RSK activity. However, 3Ac-SL0101 does not inhibit the phosphorylation of substrates associated with the kinase activity of other members of the AGC family, PKA, PKC and AKT. These data indicate that 3Ac-SL0101, like SL0101, demonstrates specificity for RSK in intact cells.

3Ac-SL0101 Preferentially Inhibits the Growth of Breast Cancer Cells

Figure 5A:
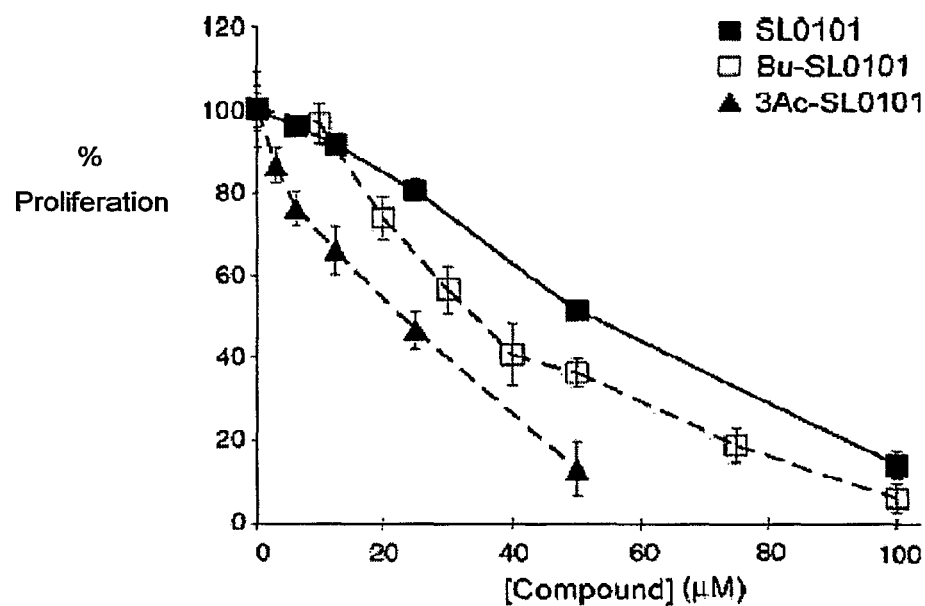
FIG. 5, comprising FIGS. 5A, 5B, and 5C, graphically illustrates that 3Ac-SL0101 selectively inhibits MCF-7 breast cancer cell proliferation, but not nontransformed breast cell proliferation. (5A) MCF-7 cells were treated with vehicle or the indicated concentration of Bu-SL0101, 3Ac-SL0101 and SL0101; (5B) MCF-7 (cancer) and MCF-10A (nontransformed) cells were treated with vehicle or the indicated concentration of Bu-SL0101; or (5C) MCF-7 and MCF-10A cells were treated with vehicle or the indicated concentration of 3Ac-SL0101. The cell number was measured after 48 h of treatment. Values given are the fold proliferation as a percentage of that observed with vehicle-treated cells. Points, mean (n=2 in quadruplicate); bars=SD.
Figure 5B:
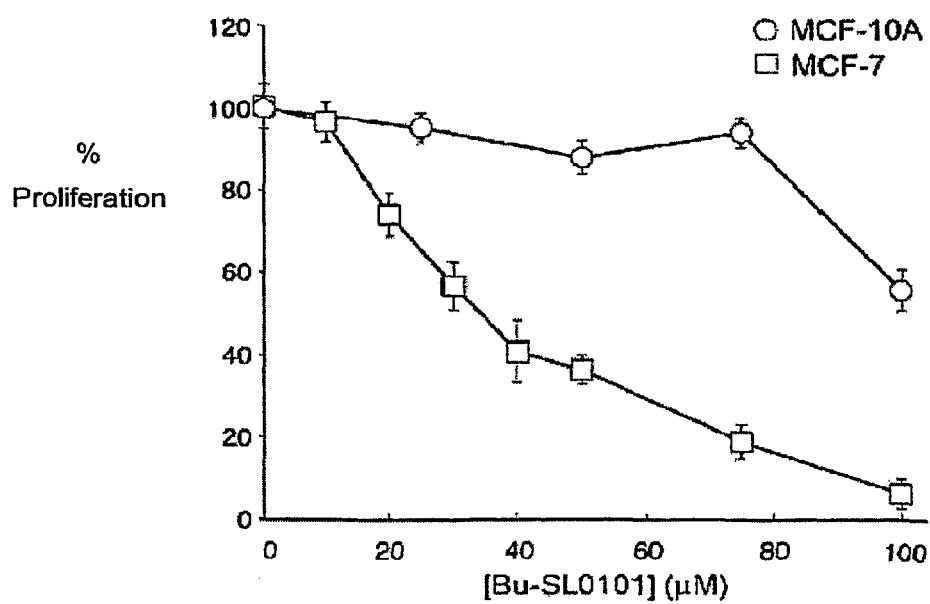
Figure 5C:
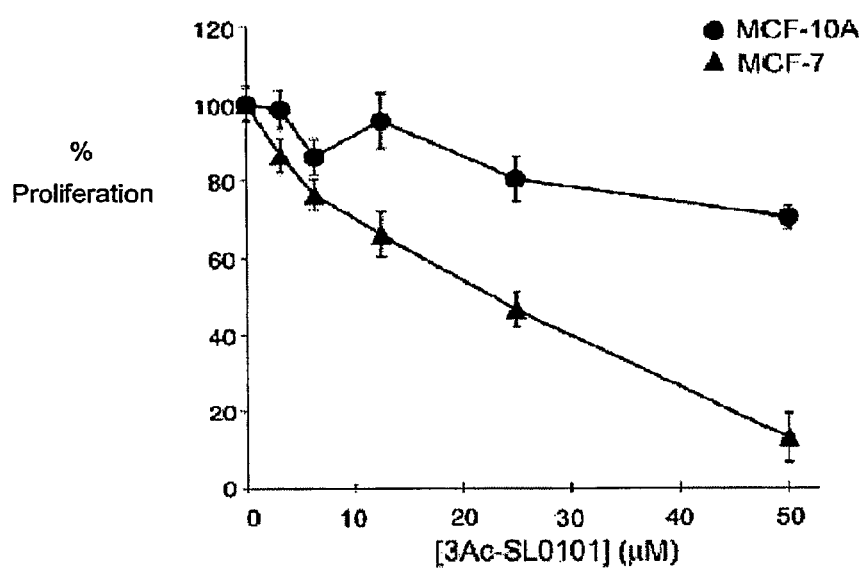
Figure 6:
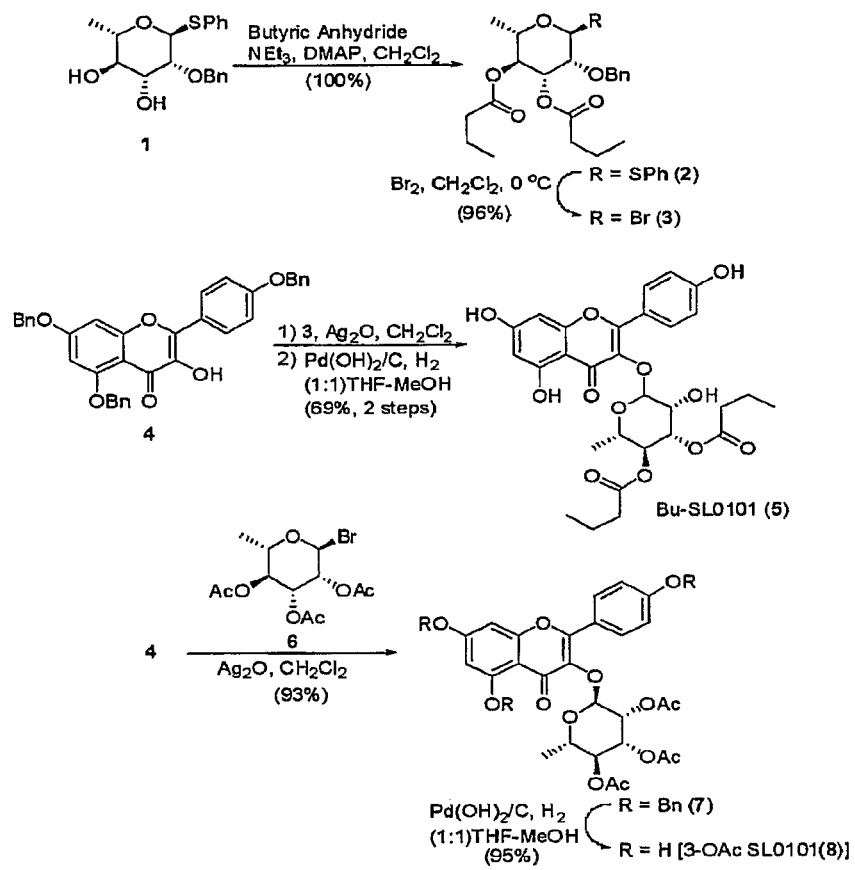
FIG. 6. Synthetic Scheme.

To test the hypothesis proposed herein that Bu-SL0101 and 3Ac-SL0101 would be more potent inhibitors in intact cells than SL0101 we determined their ability to inhibit the proliferation of MCF-7 cells. The maximum solubility of Bu-SL0101 and 3Ac-SL0101 in tissue culture media is ~100 µM and ~50 µM, respectively, notwithstanding the higher calculated LogP of Bu-SL0101 than 3Ac-SL0101. The data were fit using non-linear regression analysis. Bu-SL0101 inhibited MCF-7 proliferation with an $EC_{50}$ of 40 µM, which was only slightly lower than that obtained with SL0101 (FIG. 5A). Bu-SL0101 began to significantly inhibit MCF-10A proliferation at a concentration of 100 µM, which may reflect its ability to inhibit kinases in addition to RSK (FIG. 5B). 3Ac-SL0101 was ~2-fold more potent than SL0101 at inhibiting the growth of MCF-7 cells with an $EC_{50}$ of 25 µM (FIG. 5A). 3Ac-SL0101 did not substantially inhibit MCF-10A proliferation at concentrations that effectively inhibited MCF-7 cell growth by >80% (FIG. 5C). Thus inhibition of RSK activity parallels the decrease in MCF-7 cell proliferation;[4] further, 3Ac-SL0101 demonstrates a significantly improved inhibition of RSK activity in intact cells relative to SL0101 without any alteration in its specificity for RSK.

Discussion

The identification of RSK as a novel target for anti-breast cancer and anti-prostate cancer agents has been reported.[4,7] The identification and characterization of SL0101, an RSK-specific inhibitor isolated from *F. refracta* was previously reported.[4] SL0101 was previously found to inhibit the growth of the human breast cancer cells and human prostate cancer cells with an efficacy paralleling its ability to inhibit RSK in intact cells. However, the potency of SL0101 as a RSK inhibitor in intact cells is ~50-fold higher than its $K_i$.

The presently disclosed experiments were designed based on the hypothesis that improving cellular uptake would increase the efficacy of SL0101. Therefore, we synthesized the SL0101 analogs, Bu-SL0101 and 3Ac-SL0101, which have calculated LogP values of 4.30 and 3.07, respectively, compared to 2.56 for SL0101. 3Ac-SL0101 and SL0101 demonstrated the same specificity for inhibition of RSK activity in intact cells but Bu-SL0101 was not specific for just RSK. Thus, the range of modifications that can be introduced on the rhamnose while maintaining specificity for RSK inhibition may be limited. However, Bu-SL0101 was still effective in inhibiting cancer cell proliferation. These results are in agreement with previous results which showed that the rhamnose moiety is essential for the high affinity interaction of SL0101 with RSK.[4] Despite the >50-fold increase in hydrophobicity, the $EC_{50}$ of Bu-SL0101 for inhibition of MCF-7 proliferation was only slightly lower than that obtained for SL0101. However, the $EC_{50}$ for 3Ac-SL0101 for inhibiting MCF-7 cell proliferation was >2-fold lower than that for SL0101. Thus while increasing the hydrophobic character of the SL0101 analogs can improve their efficacy in intact cells there is not a simple correlation between LogP and $EC_{50}$ for inhibition of MCF-7 cell growth.

RSK is an unusual kinase in that it contains two non-identical kinase domains, an N-terminal kinase domain (NTKD) and a C-terminal kinase domain (CTKD) that are separated by a linker region. The NTKD most closely resembles p70 ribosomal S6 kinase and is responsible for phosphorylating exogenous substrates.[14] The CTKD most closely resembles calmodulin-dependent kinase and its only known substrate is RSK itself.[15] In response to mitogen treatment the CTKD is activated and autophosphorylation by the CTKD enhances the activity of the NTKD.[16] The major determinant of SL0101 binding specificity is a unique sequence present in the ATP-binding domain of the NTKD of RSK.[4] Thus, SL0101 acts to directly inhibit the phosphorylation of exogenous substrates via its interaction with the NTKD. SL0101 inhibits both the basal and mitogen-induced activity of the NTKD.[4]

Recently, another RSK inhibitor, a fluoromethylketone, was identified that inhibits the CTKD.[17] Pretreatment of RSK with fluoromethylketone in the absence of ATP produces an $IC_{50}$ in an in vitro kinase assay of 15 nM.[17] In intact cells, which have an intracellular ATP concentration of ~1.4 mM[18], a concentration of ~10 µM fluoromethylketone is required to completely inhibit the activity of ectopically expressed RSK for phosphorylation of histone H3[17], a nonphysiological substrate for RSK.[19,20] Inhibition of the CTKD autophosphorylation by fluoromethylketone should inhibit mitogen-induced activation of NTKD kinase activity. However, the isolated NTKD is able to phosphorylate exogenous substrates[21] and it may be that the fluoromethylketone does not inhibit the basal activity of the NTKD. Thus, by interacting with different kinase domains SL0101 and the fluoromethylketone inhibit RSK kinase activity through different mechanisms.

The molecular mechanism that results in RSK playing a dominant role in regulating proliferation in some cancer types has not yet been elucidated. It has been proposed that among the numerous events involved in tumorigenesis is an increased reliance on compromised signaling pathways as well as the dormancy of alternative signaling pathways.[22,23] thus it appears that some cancers become dependent on RSK activity, rendering the proliferation of these cells amenable to inhibition by a RSK-specific inhibitor. The growth of normal cells is presumably not dependent on RSK because intact signaling pathways provide numerous mechanisms for circumventing inhibition of a single signaling event. The identification of RSK as a novel target and the synthesis of a more potent SL0101 analog will allow the further characterization of RSK inhibitors as potential chemotherapeutic agents for breast, sarcoma, and prostate cancer.

The invention should not be construed to be limited solely to the assays and methods described herein, but should be construed to include other methods and assays as well. Other methods which were used but not described herein are well known and within the competence of one of ordinary skill in the art of chemistry, biochemistry, molecular biology, and clinical medicine. One of ordinary skill in the art will know that other assays and methods are available to perform the procedures described herein.

The abbreviations used herein have their conventional meaning within the clinical, chemical, and biological arts. In the case of any inconsistencies, the present disclosure, including any definitions therein will prevail.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations. Accordingly, the present invention is not intended to be limited to the embodiments shown herein but is to be accorded the widest scope consistent with the principles and novel features disclosed herein.

BIBLIOGRAPHY

The following references are incorporated by reference herein in their entirety:
1. Xu, Y.; Smith, J. A.; Lannigan, D. A.; Hecht, S. M. *Biorg. Med. Chem.,* 2006, 14:11:3974-3977
2. Roux, P. P.; Blenis, J. *J. Microbiol. Mol. Biol. Rev.* 2004, 68, 320-44.
3. Sebolt-Leopold, J. S. *Oncogene* 2000, 19, 6594-6595.
4. Smith, J. A.; Poteet-Smith, C. E.; Xu, Y.; Errington, T. M.; Hecht, S. M.; Lannigan, D. A. *Cancer Res.* 2005, 65, 1027-1034.
5. Joel, P. B.; Smith, J.; Sturgill, T. W.; Fisher, T. L.; Blenis, J.; Lannigan, D. A. *Mol. Cell. Biol.* 1998, 18, 1978-84.
6. Clark, D. E.; Poteet-Smith, C. E.; Smith, J. A.; Lannigan, D. A. *EMBO J.* 2001, 20, 3484-3494.
7. Clark, D. E.; Errington, T. M.; Smith, J. A.; Frierson, H. F., Jr.; Weber, M. J.; Lannigan, D. A. *Cancer Res.* 2005, 65, 3108-3116.
8. David, J. P.; Mehic, D.; Bakiri, L.; Schilling, A. F.; Mandic, V.; Priemel, M.; Idarraga, M. H.; Reschke, M. O.; Hoffmann, O.; Amling, M.; Wagner, E. F. *J. Clin. Invest.* 2005, 115, 664-672.
9. Hurbin, A.; Coll, J. L.; Dubrez-Daloz; L.; Mari, B.; Auberger, P.; Brambilla, C.; Favrot, M. C. *J. Biol. Chem.* 2005, 280, 19757-19767.
10. Cohen, P. *Nat. Rev. Drug Discovery* 2002, 1, 309-315.
11. Maloney, D. J.; Hecht, S. M. *Org. Lett.* 2005, 7, 1097-1099.
12. Morillo, M.; Lequart, V.; Grand, E.; Goethals, G.; Usubillaga, A.; Villa, P.; Martin, P. *Carbohydr. Res.* 2001, 334, 281-287.
13. Wang, X; Li, W.; Williams, M.; Terada, N.; Alessi, b. R.; Proud, C. G. *EMBO J.* 2001, 20, 4370-4379.
14. Leighton, I. A.; Dalby, K. N.; Caudwell, F. B.; Cohen, P. T.; Cohen, P. *FEBS Lett.* 1995, 375, 289-293.
15. Vik, T. A.; Ryder, J. W. *Biochem. Biophys. Res. Commun.* 1997, 235, 398-402.
16. Dalby, K. N.; Morrice, N.; Caudwell, F. B.; Avruch, J.; Cohen, P. *J. Biol Chem.* 1998, 273, 1496-1505.
17. Cohen, M. S.; Zhang, C.; Shokat, K. M.; Taunton, J. *Science* 2005, 308, 1318-1321.
18. Gribble, F. M.; Loussouarn, G.; Tucker, S. J.; Zhao, C.; Nichols, C. G.; Ashcroft, F. M. *J. Biol. Chem.* 2000, 275, 30046-30049.
19. Davie, J. R. *Sci STKE* 2003, 2003, PE33.
20. Soloaga, A.; Thomson, S.; Wiggin, G. R.; Rampersaud, N.; Dyson, M. H.; Hazzalin, C. A.; Mahadevan, L. C.; Arthur, J. S. *EMBO J.* 2003, 22, 2788-2797.
21. Richards, S. A.; Fu, J.; Romanelli, A.; Shimamura, A.; Blenis, J. *Curr. Biol.* 1999, 9, 810-820.
22. Mills, G. B.; Lu, Y.; Kohn, E. C. *Proc. Natl. Acad. Sci. U.S.A.* 2001, 98, 10031-10033.
23. Neshat, M. S.; Mellinghoff, I. K.; Tran, C.; Stiles, B.; Thomas, G.; Petersen, R.; Frost, P.; Gibbons, J. J.; Wu, H.; Sawyers, C. L. *Proc. Natl. Acad. Sid. U.S.A.* 2001, 98, 10314-10319.

What is claimed is:

1. An isolated compound represented by the general structure of formula I:

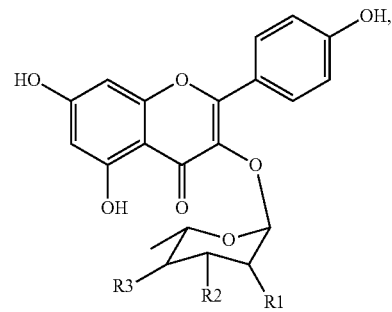

wherein
each of R1, R2, and R3 are OAc.

2. An isolated compound represented by the general structure of formula I:

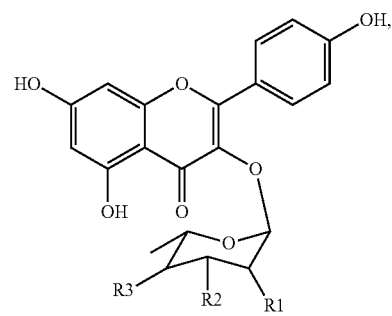

wherein
R2 and R3 are butyryl; and
R1 is OH.

* * * * *